United States Patent [19]

Agre

[11] Patent Number: 5,858,702
[45] Date of Patent: Jan. 12, 1999

[54] ISOLATION, CLONING AND EXPRESSION OF TRANSMEMBRANE WATER CHANNEL AQUAPORIN 5 (AQP5)

[75] Inventor: Peter C. Agre, Baltimore, Md.

[73] Assignee: The Johns Hopkins University, Baltimore, Md.

[21] Appl. No.: 393,996

[22] Filed: Feb. 24, 1995

Related U.S. Application Data

[63] Continuation-in-part of Ser. No. 930,168, Aug. 17, 1992, abandoned, which is a continuation-in-part of Ser. No. 806,273, Dec. 13, 1991, abandoned.

[51] Int. Cl.$^6$ .......................... C12N 15/12; C12N 15/63; C07K 14/435
[52] U.S. Cl. .................. 435/69.1; 435/320.1; 435/252.3; 536/23.5; 530/350
[58] Field of Search ................................. 536/23.4, 23.5; 435/69.1, 252.3, 320.1; 530/350

[56] References Cited

U.S. PATENT DOCUMENTS

| | | | |
|---|---|---|---|
| 4,446,128 | 5/1984 | Baschang et al. | 424/88 |
| 4,920,209 | 4/1990 | Davis et al. | 435/235 |
| 4,959,355 | 9/1990 | Fischbarg et al. | 514/23 |

OTHER PUBLICATIONS

Masu, et al., 1987, "cDNA cloning of bovine substance–K receptor through oocyte expression system", *Nature*, 329:836–838.

Denker, et al., 1988, "Identification, Purification, and Partial Characterization of a Novel M,28,000 Integral Membrane Protein from Erythrocytes and Renal Tubules", *J. Biol. Chem.*, 263:15634–15642.

Dillman, R.O., 1989, "Monoclonal Antibodies for Treating Cancer," *Ann. Int. Med.*, III:592–602.

Hird, et al., 1990, "Immunotherapy with Monoclonal Antibodies," in *Genes and Cancer*, Carney, et al., eds., John Wiley & Sons, Ltd., pp. 183–189.

Zhang et al., 1990, "Expression of mRNA Coding for Kidney and Red Cell Water Channels in *Xenopus* Oocytes", *J. Biol. Chem.*, 265:25375–15378.

Smith, et al., 1991, "Erythrocyte M$_r$28,000 Transmembrane Protein Exists As A Multisubunit Oligomer Similar to Channel Proteins," *J. Biol. Chem.*, 266:6407–6415.

Tsai, et al., 1991, "High Channel–Mediated Water Permeability in Rabbit Erythrocytes: Characterization in Native Cells and Expression in *Xenopus* Oocytes," *Biochemistry*, 30:2087–2092.

Waldmann, T.A., 1991, "Monoclonal Antibodies in Diagnosis and Therapy," *Science*, 252:1657–1662.

Preston, et al., 1991, "Isolation of the cDNA for erythrocyte integral membrane protein of 28 kilodaltons: Member of an ancient channel family", *Proc. Natl. Acad. Sci. USA*, 88:1–5.

Zeidel, et al., 1992, "Reconstruction of Functional Water Channels in Liposomes Containing Purified Red Cell CHIP28 Protein", *Biochemistry*, 31:7436–7440.

Preston, et al., 1992, "Appearance of Water Channels in *Xenopus* Oocytes Expressing Red Cell CHIP28 Protein", *Science*, 256:385–387.

Smith et al., 1994, "Human Red Cell Aquaporin CHIP:I. Molecular characterization of ABH and Colton Blood Group Antigens," *J. Clin. Investigation*, 94:1043–1049.

Agre, et al., 1994, Human Red Cell Aquaporin CHIP: II. Expression During Normal Fetal Development and in a Novel Form of Congenital Dyserythropoietic Anemia, *J. Clin. Invest.*, 204:339–340.

Chen, et al., 1986, "Human Erythrocyte Glucose Transporter: Normal Asymmetric Orientation and Function in Liposomes," *Proc. Natl. Acad. Sci., USA*, 83:2652–2656.

Agre, et al., 1993, "Aquaporin CHIP: The Archetypal Molecular Water Channel," *Am. J. Physiol*, 265:F463–F476.

Bondy, et al., 1993, "Developmental Gene Expression and Tissue Distribution of the CHIP28 Water–Channel Protein," *Proc. Natl. Acad. Sci., USA*, 90:4500–4504.

Moon, et al., 1993, "The Human Aquaporin–CHIP Gene," *J. Biol. Chem.*, 268:15772–15778.

Nielsen, et al., 1993, "Distribution of the Aquaporin CHIP in Secretory and Resorptive Epithelia and Capillary Endothelia," *Proc. Natl. Acad. Sci., USA*, 90:7275–7279.

Nielsen, et al., 1993, "CHIP28 Water Channels are Localized in Constitutively Water–Permeable Segments of the Nephron," *J. Cell Biol.*, 120:371–383.

Preston, et al., 1993, "The Mercury–Sensitive Residue at Cysteine 189 in the CHIP28 Water Channel," *J. Biol. Chem.*, 268:17–20.

Smith, et al., 1993, "Concurrent Expression of Erythroid and Renal Aquaporin CHIP and Appearance of Water Channel Activity in Perinatal Rats," *J. Clin. Invest.*, 92:2035–2041.

Jung, et al., 1994, "Molecular Characterization of an Aquaporin cDNA from Brain: Candidate Osmoreceptor and Regulator of Water Balance," *Proc. Natl. Acad. Sci., USA*, 91:13052–13056.

Preston, et al., 1994, "Membrane Topology of Aquaporin CHIP," *J. Biol. Chem.*, 269:1668–1673.

(List continued on next page.)

*Primary Examiner*—Stephen Walsh
*Assistant Examiner*—Daryl A. Basham
*Attorney, Agent, or Firm*—Banner & Witcoff, Ltd.

[57] ABSTRACT

A transmembrane water channel protein is isolated in highly purified form from human erythrocytes. An identical protein is also found in kidney tubules. cDNA encoding this protein has been isolated and its amino acid sequence determined. cDNA encoding a transmembrane water channel protein has also been obtained from salivary gland, and an identical protein is found in lacrimal gland, cornea, and lung tissue. The amino acid sequence of the protein has been deduced from the cDNA, and the protein has been designated Aquaporin-5. Using the nucleic acid or protein sequence provided herein, the protein may be produced by recombinant DNA techniques. Expression of the protein may be determined by either immunoassay or in situ hybridization assay.

5 Claims, 20 Drawing Sheets

OTHER PUBLICATIONS

Preston, et al., 1994, "Mutations in Aquaporin–1 in Phenotypically Normal Humans Without Functional CHIP Water Channels," *Science,* 265:1585–1587.

Walz, et al., 1994, "Biologically Active Two–Dimensional Crystals of Aquaporin CHIP," *J. Biol. Chem.,* 269:1583–1586.

Zeidel, et al., 1994, "Ultrastructure, Pharmacologic Inhibition, and Transport Selectivity of Aquaporin Channel–Forming Integral Protein in Proteoliposomes," *Biochemistry,* 33:1606–1615.

Rains, et al., 1995, "Molecular Cloning and Characterization of an Aquaporin cDNA from Salivary, Lacimal, and Respiratory Tissues," *J. Biol. Chem.,* 270:1908–1912.

FIG. 2

```
 -38                        GCACCCGGCAGCGGTCTCAGGCCAAGCCCCCTGCCAGC  -1
   1 ATGGCCAGCGAGTTCAAGAAGAAGCTCTTCTGGAGGGCAGTGGTGGCCGAGTTCCTGGCC  60
   1 M   A   S   E   F   K   K   K   L   F   W   R   A   V   V   A   E   F   L   A   20
  61 ACGACCCTCTTTGTCTTCATCAGCATCGGTTCTGCCCTGGGCTTCAAATACCCGGTGGGG 120
  21 T   T   L   F   V   F   I   S   I   G (S)  A   L   G   F   K   Y   P   V   G   40
 121 AACAACCAGACGGCGGTCCAGGACAACGTGAAGGTGTCGCTGGCCTTCGGGCTGAGCATC 180
  41 N   N   Q   T   A   V   Q   D   N   V   K   V   S   L   A   F   G   L   S   I   60
 181 GCCACGCTGGCGCAGAGTGTGGGCCACATCAGCGGCGCCCACCTCAACCCGGCTGTCACA 240
  61 A   T   L   A   Q   S   V   G   H   I   S   G   A   H   L   N   P   A   V   T   80
 241 CTGGGGCTGCTGCTCAGCTGCCAGATCAGCATCTTCCGTGCCCTCATGTACATCATCGCC 300
  81 L   G   L   L   L   S   C   Q   I   S   I   F   R   A   L   M   Y   I   I   A  100
 301 CAGTGCGTGGGGGCCATCGTCGCCACCGCCATCCTCTCAGGCATCACCTCCTCCCTGACT 360
 101 Q   C   V   G   A   I   V   A   T   A   I   L   S   G   I   T   S   S   L   T  120
 361 GGGAACTCGCTTGGCCGCAATGACCTGGCTGATGGTGTGAACTCGGGCCAGGGCCTGGGC 420
 121 G   N   S   L   G   R   N   D   L   A   D   G   V   N   S   G   Q   G   L   G  140
 421 ATCGAGATCATCGGGACCCTCCAGCTGGTGCTATGCGTGCTGGCTACTACCGACCGGAGG 480
 141 I   E   I   I   G   T   L   Q   L   V   L   C   V   L   A   T   T   D   R   R  160
 481 CGCCGTGACCTTGGTGGCTCAGCCCCCCTTGCCATCGGCCTCTCTGTAGCCCTTGGACAC 540
 161 R   R   D   L   G   G   S   A   P   L   A   I   G   L   S   V   A   L   G   H  180
 541 CTCCTGGCTATTGACTACACTGGCTGTGGGATTAACCCTGCTCGGTCCTTTGGCTCCGCG 600
 181 L   L   A   I   D   Y   T   G   C   G   I   N   P   A   R   S   F   G   S   A  200
 601 GTGATCACACACAACTTCAGCAACCACTGGATTTTCTGGGTGGGGCCATTCATCGGGGGA 660
 201 V   I   T   H   N   F   S   N   H   W   I   F   W   V   G   P   F   I   G   G  220
 661 GCCCTGGCTGTACTCATCTACGACTTCATCCTGGCCCCACGCAGCAGTGACCTCACAGAC 720
 221 A   L   A   V   L   I   Y   D   F   I   L   A   P   R   S   S   D   L   T   D  240
 721 CGCGTGAAGGTGTGGACCAGCGGCCAGGTGGAGGAGTATGACCTGGATGCCGACGACATC 780
 241 R   V   K   V   W   T   S   G   Q   V   E   E   Y   D   L   D   A   D   D   I  260
 781 AACTCCAGGGTGGAGATGAAGCCCAAATAGAAGGGGTCTGGCCCGGGCATCCACGTAGGG 840
 261 N   S   R   V   E   M   K   P   K ...                                         269
 841 GGCAGGGGCAGGGGCGGGCGGAGGGAGGGGAGGGGTGAAATCCATACTGTAGACACTCTG 900
 901 ACAAGCTGGCCAAAGTCACTTCCCCAAGATCTGCCAGACCTGCATGGTCAAGCCTCTTAT 960
 961 GGGGGTGTTTCTATCTCTTTCTTTCTCTTTCTGTTTCCTGGCCTCAGAGCTTCCTGGGGA 1020
1021 CCAAGATTTACCAATTCACCCACTCCCTTGAAGTTGTGGAGGAGGTGAAAGAAAGGGACC 1080
1081 CACCTGCTAGTCGCCCCTCAGAGCATGATGGGAGGTGTGCCAGAAAGTCCCCCCTCGCCC 1140
1141 CAAAGTTGCTCACCGACTCACCTGCGCAAGTGCCTGGGATTCTACCGTAATTGCTTTGTG 1200
1201 CCTTTGGGCACGGCCCTCCTTCTTTTCCTAACATGCACCTTGCTCCCAATGGTGCTTGGA 1260
1261 GGGGGAAGAGATCCCAGGAGGTGCAGTGGAGGGGGCAAGCTT                   1302
. . . . . . . . . . . . . . . . . . . . . . . . . . . . . . . . . . . . . . . . .
   1 AACCAAGGCCCTGTCTCTGGCTACTCCCTGGACCACGAGGCTGATTCCTCTCATTTCCAG  60
  61 CTTCTCAGTTTCTGCCTGGGCAATGCCAGGGGCCAGGAGTGGGGAGAGTTGTGATGGAGG 120
 121 GGAGAGGGGTCACACCCACCCCCTGCCTGGTTCTAGGCTGCTGCACACCAAGGCCCTGCA 180
 181 TCTGTCTGCTCTGCATATATGTCTCTTTGGAGTTGGAATTTCATTATATGTTAAGAAAAT 240
 241 AAAGGAAAATGACTTGTAAGGTCAAAAAAAAAAAAA                         276
```

FIG. 14A

```
 -109                            GGCACGAGGCACCGCGCGCAGAGCCCCGCAGACAGACGCCCGCCGCTAC
  -60   CAGCGCCGCCCCGACGGCCGCCCCGCAACCCTCCCGCTGCCACCGGGCCCCCAAGGCACC
    1   ATGAAAAAGGAGGTGTGCTCCCTTGCCTTCTTCAAGGCGGTGTTCGCAGAGTTCCTGGCC
    1    M  K  K  E  V  C  S  L  A  F  F  K  A  V  F  A  E  F  L  A
   61   ACCCTCATCTTCGTCTTCTTTGGCCTGGGCTCAGCACTCAAGTGGCCCTCGGCTCTGCCC
   21    T  L  I  F  V  F  F  G  L  G  S  A  L  K  W  P  S  A  L  P
  121   ACCATTCTGCAAATCTCAATTGCCTTTGGCCTGGCCATAGGTACCTTAGCCCAAGCTCTG
   41    T  I  L  Q  I  S  I  A  F  G  L  A  I  G  T  L  A  Q  A  L
  181   GGACCTGTGAGTGGTGGCCACATCAATCCAGCCATTACTCTGGCCCTCTTAATAGGAAAC
   61    G  P  V  S  G  G  H  I [N  P  A] I  T  L  A  L  L  I  G  N
  241   CAGATCTCGCTGCTCCGAGCTGTCTTCTACGTGGCAGCCCAGCTGGTGGGCGCCATTGCT
   81    Q  I  S  L  L  R  A  V  F  Y  V  A  A  Q  L  V  G  A  I  A
  301   GGGGCAGGCATCCTGTACTGGCTGGCGCCACTCAATGCCCGGGGTAACCTGGCCGTCAAT
  101    G  A  G  I  L  Y  W  L  A  P  L  N  A  R  G  N  L  A  V  N
  361   GCGCTGAACAACAACACAACGCCTGGCAAGGCCATGGTGGTGGAGTTAATCTTGACTTTC
  121    A  L  N  N* N* T  T  P  G  K  A  M  V  V  E  L  I  L  T  F
  421   CAGCTAGCCCTCTGCATCTTCTCCTCCACCGACTCTCGCCGAACCAGCCCTGTGGGCTCC
  141    Q  L  A  L  C  I  F  S  S  T  D [S  R  R  T  S] P  V  G  S
  481   CCAGCCTTATCCATTGGCTTGTCTGTCACACTGGGCCATCTTGTGGGGATCTACTTCACC
  161    P  A  L  S  I  G  L  S  V  T  L  G  H  L  V  G  I  Y  F  T
  541   GGCTGTTCCATGAACCCAGCCCGATCTTTCGGCCCTGCGGTGGTCATGAACCGGTTCAGC
  181    G  C  S  M [N  P  A] R  S  F  G  P  A  V  V  M  N  R  F  S
  601   CCCTCTCACTGGGTCTTCTGGGTAGGGCCTATTGTGGGGGCCATGCTGGCGGCCATCCTC
  201    P  S  H  W  V  F  W  V  G  P  I  V  G  A  M  L  A  A  I  L
  661   TATTTCTACCTGCTCTTCCCCTCCTCTCTGAGCCTCCATGATCGCGTGGCTGTCGTCAAA
  221    Y  F  Y  L  L  F  P  S  S  L  S  L  H  D  R  V  A  V  V  K
  721   GGCACATATGAGCCGGAGGAGGACTGGGAAGATCATCGAGAGGAGAGGAAGAAGACCATC
  241    G  T  Y  E  P  E  E  D  W  E  D  H  R  E  E  R  K  K  T  I
  781   GAGCTGACGGCACACTGACTGGTGCCGGACAGGGGCCAGTCCCTCAGCCCCTGGACCACT
  261    E  L  T  A  H ...
  841   GGAGAAAAGGAAGACGAAGAGTTTGAAGCACCCCTCCCCAACATCCTCTCAGCTGGGGAA
  901   GAGGCATTGGATCCCCATGCTGCTGCACAGGGACAGGAGCAGAAGCCCATAATGGGACAC
  961   TTGGGTGTGGGCCAAGGGCTGGAGTCTGACAGGGTCAGGGACATAGCCGCTTTGGAATCA
 1021   GGCAGAATGTCTGCCACAGCTCAGACCTCAGAGATTCGTGAATGCGGTGCCAAGCTCACA
 1081   GGCGGTCCAGGACCACACCAGAAAGGGACGACAGCTTGCTTATCTCTCCCAACCCAGTAT
 1141   CTCAAGTGCCAAAGCCGGCCCCCAGGTGGACAGAGGGGACATTTCCCCCAGAGCTCTTCA
 1201   GGAGAGGGATAGATGGCTCACGGAGTGCTATTTTATTTATTTCTGGTCAAGGATGGGGGT
 1261   GGGGTGGGGCTGCTGGTGTTTGAGCTGGCGCTTCCCAATAAACCACCTATCTTCAAAAAA
 1321   AAAAAAAAAAAAA
```

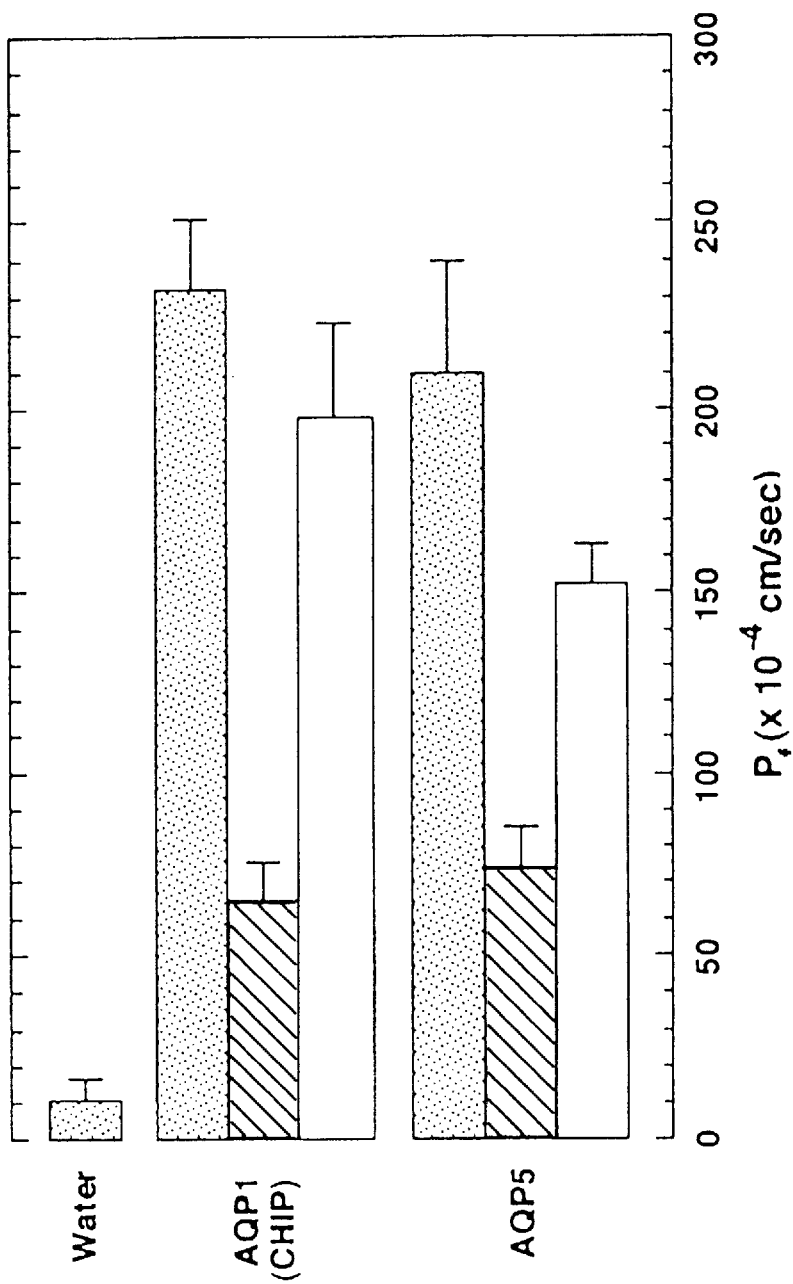

FIG. 17A
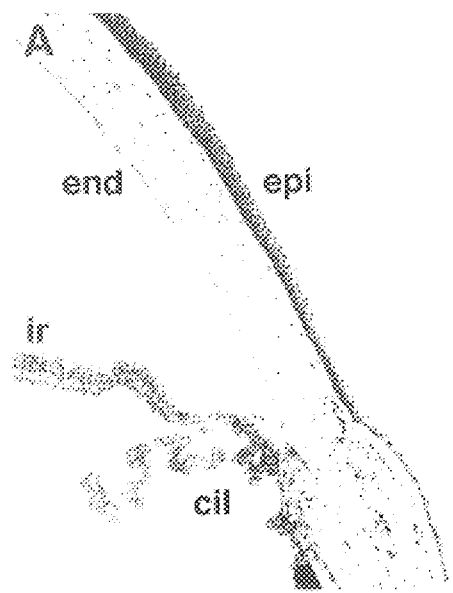
FIG. 17A'  FIG. 17A"
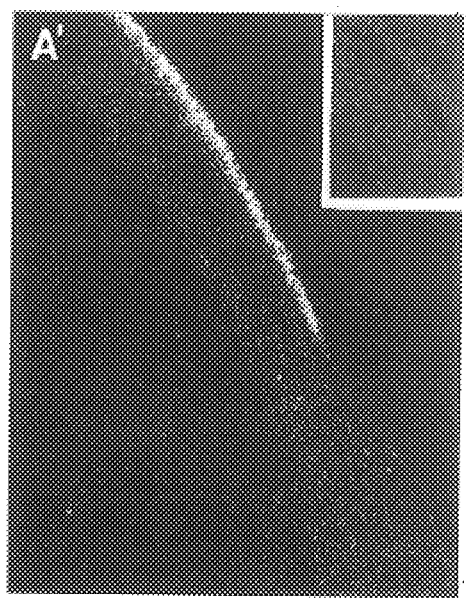

FIG. 17B"

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ala  Ser  Glu  Phe  Lys  Lys  Lys  Leu  Phe  Trp  Arg  Ala  Val  Val  Ala  Glu
 1              5                        10                       15

Phe  Leu  Ala  Thr  Thr  Leu  Phe  Val  Phe  Ile  Ser  Ile  Gly  Xaa  Ala  Leu
               20                        25                       30

Gly  Phe  Lys
          35
```

( 2 ) INFORMATION FOR SEQ ID NO:2:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Trp  Glu  Leu  Arg  Ser  Ala  Ser  Phe  Trp  Arg  Ala  Ile  Cys  Ala  Glu
 1              5                        10                       15

Phe  Phe  Ala  Ser  Leu  Phe  Tyr  Val  Phe  Phe  Gly  Leu  Gly  Ala  Ser  Leu
               20                        25                       30

Arg  Trp  Ala
          35
```

( 2 ) INFORMATION FOR SEQ ID NO:3:

( i ) SEQUENCE CHARACTERISTICS:
    ( A ) LENGTH: 31 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:3:

CTTCTAGATT CTGGAGGGCC GTSGTSGCNG A  31

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Phe Trp Arg Ala Val Val Ala Glu
   1        5

( 2 ) INFORMATION FOR SEQ ID NO:5:

( i ) SEQUENCE CHARACTERISTICS:
    ( A ) LENGTH: 29 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:5:

TAATCGATCC CRATRSWRAT RAASACRAA  29

( 2 ) INFORMATION FOR SEQ ID NO:6:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

Phe Val Phe Ile Ser Ile Gly
   1       5

( 2 ) INFORMATION FOR SEQ ID NO:7:

( i ) SEQUENCE CHARACTERISTICS:
    ( A ) LENGTH: 30 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:7:

GCTCTAGAAG AGGGTCGTGG CCAGGAACTC  30

( 2 ) INFORMATION FOR SEQ ID NO:8:

( i ) SEQUENCE CHARACTERISTICS:

(A) LENGTH: 30 base pairs
(B) TYPE: nucleic acid
(C) STRANDEDNESS: unknown
(D) TOPOLOGY: unknown (i i) MOLECULE TYPE: DNA (genomic)

(x i) SEQUENCE DESCRIPTION: SEQ ID NO:8:

GCTCTAGAGT TCAAGAAGAA GCTCTTCTGG 30

(2) INFORMATION FOR SEQ ID NO:9:

(i) SEQUENCE CHARACTERISTICS:
(A) LENGTH: 31 base pairs
(B) TYPE: nucleic acid
(C) STRANDEDNESS: unknown
(D) TOPOLOGY: unknown (i i) MOLECULE TYPE: DNA (genomic)

(x i) SEQUENCE DESCRIPTION: SEQ ID NO:9:

CGGGATCCTC TTCTGGAGGG CAGTGGTGGC C 31

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: unknown
(D) TOPOLOGY: unknown (i i) MOLECULE TYPE: DNA (genomic)

(x i) SEQUENCE DESCRIPTION: SEQ ID NO:10:

GGTGGCGACG ACTCCTGGAG CCCC 24

(2) INFORMATION FOR SEQ ID NO:11:

(i) SEQUENCE CHARACTERISTICS:
(A) LENGTH: 24 base pairs
(B) TYPE: nucleic acid
(C) STRANDEDNESS: unknown
(D) TOPOLOGY: unknown (i i) MOLECULE TYPE: DNA (genomic)

(x i) SEQUENCE DESCRIPTION: SEQ ID NO:11:

TTGACACCAG ACCAACTGGT AATG 24

(2) INFORMATION FOR SEQ ID NO:12:

(i) SEQUENCE CHARACTERISTICS:
(A) LENGTH: 23 base pairs
(B) TYPE: nucleic acid
(C) STRANDEDNESS: unknown
(D) TOPOLOGY: unknown (i i) MOLECULE TYPE: DNA (genomic)

(x i) SEQUENCE DESCRIPTION: SEQ ID NO:12:

STBGGNCAYR TBAGYGGNGC NCA 23

(2) INFORMATION FOR SEQ ID NO:13:

(i) SEQUENCE CHARACTERISTICS:
(A) LENGTH: 30 base pairs
(B) TYPE: nucleic acid
(C) STRANDEDNESS: unknown
(D) TOPOLOGY: unknown ( i i ) MOLECULE TYPE: DNA (genomic)

( x i ) SEQUENCE DESCRIPTION: SEQ ID NO:13:

GGGATCCGCH CAYNTNAAYC CHGYNGTNAC 30

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

GCDGRNSCVA RDGANCGNGC NGG 23

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

CGGAATTCGD GCDGGRTTNA TNSHNSMNCC 30

( 2 ) INFORMATION FOR SEQ ID NO:16:

( i ) SEQUENCE CHARACTERISTICS:
        ( A ) LENGTH: 1340 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 39..845

( x i ) SEQUENCE DESCRIPTION: SEQ ID NO:16:

```
GCACCCGGCA  GCGGTCTCAG  GCCAAGCCCC  CTGCCAGC ATG  GCC  AGC  GAG  TTC         53
                                             Met  Ala  Ser  Glu  Phe
                                              1                    5

AAG  AAG  AAG  CTC  TTC  TGG  AGG  GCA  GTG  GTG  GCC  GAG  TTC  CTG  GCC  ACG   101
Lys  Lys  Lys  Leu  Phe  Trp  Arg  Ala  Val  Val  Ala  Glu  Phe  Leu  Ala  Thr
               10                    15                      20

ACC  CTC  TTT  GTC  TTC  ATC  AGC  ATC  GGT  TCT  GCC  CTG  GGC  TTC  AAA  TAC   149
Thr  Leu  Phe  Val  Phe  Ile  Ser  Ile  Gly  Ser  Ala  Leu  Gly  Phe  Lys  Tyr
               25                    30                      35

CCG  GTG  GGG  AAC  AAC  CAG  ACG  GCG  GTC  CAG  GAC  AAC  GTG  AAG  GTG  TCG   197
Pro  Val  Gly  Asn  Asn  Gln  Thr  Ala  Val  Gln  Asp  Asn  Val  Lys  Val  Ser
               40                    45                      50

CTG  GCC  TTC  GGG  CTG  AGC  ATC  GCC  ACG  CTG  GCG  CAG  AGT  GTG  GGC  CAC   245
Leu  Ala  Phe  Gly  Leu  Ser  Ile  Ala  Thr  Leu  Ala  Gln  Ser  Val  Gly  His
     55                    60                      65

ATC  AGC  GGC  GCC  CAC  CTC  AAC  CCG  GCT  GTC  ACA  CTG  GGG  CTG  CTG  CTC   293
Ile  Ser  Gly  Ala  His  Leu  Asn  Pro  Ala  Val  Thr  Leu  Gly  Leu  Leu  Leu
70                    75                      80                          85

AGC  TGC  CAG  ATC  AGC  ATC  TTC  CGT  GCC  CTC  ATG  TAC  ATC  ATC  GCC  CAG   341
Ser  Cys  Gln  Ile  Ser  Ile  Phe  Arg  Ala  Leu  Met  Tyr  Ile  Ile  Ala  Gln
               90                    95                      100
```

| | | | | | | | | | | | | | | | | |
|---|---|---|---|---|---|---|---|---|---|---|---|---|---|---|---|---|
| TGC | GTG | GGG | GCC | ATC | GTC | GCC | ACC | GCC | ATC | CTC | TCA | GGC | ATC | ACC | TCC | 389 |
| Cys | Val | Gly | Ala | Ile | Val | Ala | Thr | Ala | Ile | Leu | Ser | Gly | Ile | Thr | Ser | |
| | | 105 | | | | 110 | | | | | | 115 | | | | |
| TCC | CTG | ACT | GGG | AAC | TCG | CTT | GGC | CGC | AAT | GAC | CTG | GCT | GAT | GGT | GTG | 437 |
| Ser | Leu | Thr | Gly | Asn | Ser | Leu | Gly | Arg | Asn | Asp | Leu | Ala | Asp | Gly | Val | |
| | | 120 | | | | | 125 | | | | | 130 | | | | |
| AAC | TCG | GGC | CAG | GGC | CTG | GGC | ATC | GAG | ATC | ATC | GGG | ACC | CTC | CAG | CTG | 485 |
| Asn | Ser | Gly | Gln | Gly | Leu | Gly | Ile | Glu | Ile | Ile | Gly | Thr | Leu | Gln | Leu | |
| | | 135 | | | | | 140 | | | | | 145 | | | | |
| GTG | CTA | TGC | GTG | CTG | GCT | ACT | ACC | GAC | CGG | AGG | CGC | CGT | GAC | CTT | GGT | 533 |
| Val | Leu | Cys | Val | Leu | Ala | Thr | Thr | Asp | Arg | Arg | Arg | Arg | Asp | Leu | Gly | |
| 150 | | | | | 155 | | | | | 160 | | | | | 165 | |
| GGC | TCA | GCC | CCC | CTT | GCC | ATC | GGC | CTC | TCT | GTA | GCC | CTT | GGA | CAC | CTC | 581 |
| Gly | Ser | Ala | Pro | Leu | Ala | Ile | Gly | Leu | Ser | Val | Ala | Leu | Gly | His | Leu | |
| | | | | 170 | | | | | 175 | | | | | 180 | | |
| CTG | GCT | ATT | GAC | TAC | ACT | GGC | TGT | GGG | ATT | AAC | CCT | GCT | CGG | TCC | TTT | 629 |
| Leu | Ala | Ile | Asp | Tyr | Thr | Gly | Cys | Gly | Ile | Asn | Pro | Ala | Arg | Ser | Phe | |
| | | | 185 | | | | | 190 | | | | | 195 | | | |
| GGC | TCC | GCG | GTG | ATC | ACA | CAC | AAC | TTC | AGC | AAC | CAC | TGG | ATT | TTC | TGG | 677 |
| Gly | Ser | Ala | Val | Ile | Thr | His | Asn | Phe | Ser | Asn | His | Trp | Ile | Phe | Trp | |
| | | 200 | | | | | 205 | | | | | 210 | | | | |
| GTG | GGG | CCA | TTC | ATC | GGG | GGA | GCC | CTG | GCT | GTA | CTC | ATC | TAC | GAC | TTC | 725 |
| Val | Gly | Pro | Phe | Ile | Gly | Gly | Ala | Leu | Ala | Val | Leu | Ile | Tyr | Asp | Phe | |
| | | 215 | | | | | 220 | | | | | 225 | | | | |
| ATC | CTG | GCC | CCA | CGC | AGC | AGT | GAC | CTC | ACA | GAC | CGC | GTG | AAG | GTG | TGG | 773 |
| Ile | Leu | Ala | Pro | Arg | Ser | Ser | Asp | Leu | Thr | Asp | Arg | Val | Lys | Val | Trp | |
| 230 | | | | | 235 | | | | | 240 | | | | | 245 | |
| ACC | AGC | GGC | CAG | GTG | GAG | GAG | TAT | GAC | CTG | GAT | GCC | GAC | GAC | ATC | AAC | 821 |
| Thr | Ser | Gly | Gln | Val | Glu | Glu | Tyr | Asp | Leu | Asp | Ala | Asp | Asp | Ile | Asn | |
| | | | | 250 | | | | | 255 | | | | | 260 | | |
| TCC | AGG | GTG | GAG | ATG | AAG | CCC | AAA | TAGAAGGGGT | CTGGCCCGGG | CATCCACGTA | | | | | | 875 |
| Ser | Arg | Val | Glu | Met | Lys | Pro | Lys | | | | | | | | | |
| | | | | 265 | | | | | | | | | | | | |

```
GGGGGCAGGG GCAGGGGCGG GCGGAGGGAG GGGAGGGGTG AAATCCATAC TGTAGACACT        935
CTGACAAGCT GGCCAAAGTC ACTTCCCCAA GATCTGCCAG ACCTGCATGG TCAAGCCTCT        995
TATGGGGGTG TTTCTATCTC TTTCTTTCTC TTTCTGTTTC CTGGCCTCAG AGCTTCCTGG       1055
GGACCAAGAT TTACCAATTC ACCCACTCCC TTGAAGTTGT GGAGGAGGTG AAAGAAGGG        1115
ACCCACCTGC TAGTCGCCCC TCAGAGCATG ATGGGAGGTG TGCCAGAAAG TCCCCCCTCG       1175
CCCCAAAGTT GCTCACCGAC TCACCTGCGC AAGTGCCTGG GATTCTACCG TAATTGCTTT       1235
GTGCCTTTGG GCACGGCCCT CCTTCTTTTC CTAACATGCA CCTTGCTCCC AATGGTGCTT       1295
GGAGGGGGAA GAGATCCCAG GAGGTGCAGT GGAGGGGCA AGCTT                       1340
```

( 2 ) INFORMATION FOR SEQ ID NO:17:

( i ) SEQUENCE CHARACTERISTICS:
        ( A ) LENGTH: 269 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | | |
|---|---|---|---|---|---|---|---|---|---|---|---|---|---|---|---|
| Met | Ala | Ser | Glu | Phe | Lys | Lys | Lys | Leu | Phe | Trp | Arg | Ala | Val | Val | Ala |
| 1 | | | | 5 | | | | | 10 | | | | | 15 | |
| Glu | Phe | Leu | Ala | Thr | Thr | Leu | Phe | Val | Phe | Ile | Ser | Ile | Gly | Ser | Ala |
| | | | | 20 | | | | | 25 | | | | | 30 | |
| Leu | Gly | Phe | Lys | Tyr | Pro | Val | Gly | Asn | Asn | Gln | Thr | Ala | Val | Gln | Asp |

```
                        3 5                           4 0                            4 5

Asn   Val   Lys   Val   Ser   Leu   Ala   Phe   Gly   Leu   Ser   Ile   Ala   Thr   Leu   Ala
            5 0                           5 5                            6 0

Gln   Ser   Val   Gly   His   Ile   Ser   Gly   Ala   His   Leu   Asn   Pro   Ala   Val   Thr
6 5                           7 0                           7 5                            8 0

Leu   Gly   Leu   Leu   Leu   Ser   Cys   Gln   Ile   Ser   Ile   Phe   Arg   Ala   Leu   Met
                        8 5                           9 0                            9 5

Tyr   Ile   Ile   Ala   Gln   Cys   Val   Gly   Ala   Ile   Val   Ala   Thr   Ala   Ile   Leu
                  1 0 0                         1 0 5                        1 1 0

Ser   Gly   Ile   Thr   Ser   Ser   Leu   Thr   Gly   Asn   Ser   Leu   Gly   Arg   Asn   Asp
            1 1 5                         1 2 0                        1 2 5

Leu   Ala   Asp   Gly   Val   Asn   Ser   Gly   Gln   Gly   Leu   Gly   Ile   Glu   Ile   Ile
1 3 0                         1 3 5                        1 4 0

Gly   Thr   Leu   Gln   Leu   Val   Leu   Cys   Val   Leu   Ala   Thr   Thr   Asp   Arg   Arg
1 4 5                         1 5 0                        1 5 5                        1 6 0

Arg   Arg   Asp   Leu   Gly   Gly   Ser   Ala   Pro   Leu   Ala   Ile   Gly   Leu   Ser   Val
                        1 6 5                         1 7 0                        1 7 5

Ala   Leu   Gly   His   Leu   Leu   Ala   Ile   Asp   Tyr   Thr   Gly   Cys   Gly   Ile   Asn
                  1 8 0                         1 8 5                        1 9 0

Pro   Ala   Arg   Ser   Phe   Gly   Ser   Ala   Val   Ile   Thr   His   Asn   Phe   Ser   Asn
            1 9 5                         2 0 0                        2 0 5

His   Trp   Ile   Phe   Trp   Val   Gly   Pro   Phe   Ile   Gly   Gly   Ala   Leu   Ala   Val
2 1 0                         2 1 5                        2 2 0

Leu   Ile   Tyr   Asp   Phe   Ile   Leu   Ala   Pro   Arg   Ser   Ser   Asp   Leu   Thr   Asp
2 2 5                         2 3 0                        2 3 5                        2 4 0

Arg   Val   Lys   Val   Trp   Thr   Ser   Gly   Gln   Val   Glu   Glu   Tyr   Asp   Leu   Asp
                        2 4 5                         2 5 0                        2 5 5

Ala   Asp   Asp   Ile   Asn   Ser   Arg   Val   Glu   Met   Lys   Pro   Lys
                  2 6 0                         2 6 5
```

( 2 ) INFORMATION FOR SEQ ID NO:18:

( i ) SEQUENCE CHARACTERISTICS:
        ( A ) LENGTH: 1442 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 110..904

( x i ) SEQUENCE DESCRIPTION: SEQ ID NO:18:

```
GGCACGAGGC   ACCGCGCGCA   GAGCCCCGCA   GACAGACGCC   CGCCGCTACC   AGCGCCGCCC              6 0

CGACGGCCGC   CCCGCAACCC   TCCCGCTGCC   ACCGGGCCCC   CAAGGCACC ATG AAA                    1 1 5
                                                              Met Lys
                                                               1

AAG GAG GTG TGC TCC CTT GCC TTC TTC AAG GCG GTG TTC GCA GAG TTC                         1 6 3
Lys Glu Val Cys Ser Leu Ala Phe Phe Lys Ala Val Phe Ala Glu Phe
          5                   1 0                  1 5

CTG GCC ACC CTC ATC TTC GTC TTC TTT GGC CTG GGC TCA GCA CTC AAG                         2 1 1
Leu Ala Thr Leu Ile Phe Val Phe Phe Gly Leu Gly Ser Ala Leu Lys
      2 0                  2 5                  3 0

TGG CCC TCG GCT CTG CCC ACC ATT CTG CAA ATC TCA ATT GCC TTT GGC                         2 5 9
Trp Pro Ser Ala Leu Pro Thr Ile Leu Gln Ile Ser Ile Ala Phe Gly
3 5                    4 0                  4 5                  5 0

CTG GCC ATA GGT ACC TTA GCC CAA GCT CTG GGA CCT GTG AGT GGT GGC                         3 0 7
```

-continued

```
Leu Ala Ile Gly Thr Leu Ala Gln Ala Leu Gly Pro Val Ser Gly Gly
             55                  60                  65

CAC ATC AAT CCA GCC ATT ACT CTG GCC CTC TTA ATA GGA AAC CAG ATC         355
His Ile Asn Pro Ala Ile Thr Leu Ala Leu Leu Ile Gly Asn Gln Ile
             70                  75                  80

TCG CTC CTC CGA GCT GTC TTC TAC GTG GCA GCC CAG CTG GTG GGC GCC         403
Ser Leu Leu Arg Ala Val Phe Tyr Val Ala Ala Gln Leu Val Gly Ala
             85                  90                  95

ATT GCT GGG GCA GGC ATC CTG TAC TGG CTG GCG CCA CTC AAT GCC CGG         451
Ile Ala Gly Ala Gly Ile Leu Tyr Trp Leu Ala Pro Leu Asn Ala Arg
            100                 105                 110

GGT AAC CTG GCC GTC AAT GCG CTG AAC AAC AAC ACA ACG CCT GGC AAG         499
Gly Asn Leu Ala Val Asn Ala Leu Asn Asn Asn Thr Thr Pro Gly Lys
115                 120                 125                 130

GCC ATG GTG GTG GAG TTA ATC TTG ACT TTC CAG CTA GCC CTC TGC ATC         547
Ala Met Val Val Glu Leu Ile Leu Thr Phe Gln Leu Ala Leu Cys Ile
            135                 140                 145

TTC TCC TCC ACC GAC TCT CGC CGA ACC AGC CCT GTG GGC TCC CCA GCC         595
Phe Ser Ser Thr Asp Ser Arg Arg Thr Ser Pro Val Gly Ser Pro Ala
            150                 155                 160

TTA TCC ATT GGC TTG TCT GTC ACA CTG GGC CAT CTT GTG GGG ATC TAC         643
Leu Ser Ile Gly Leu Ser Val Thr Leu Gly His Leu Val Gly Ile Tyr
            165                 170                 175

TTC ACC GGC TGT TCC ATG AAC CCA GCC CGA TCT TTC GGC CCT GCG GTG         691
Phe Thr Gly Cys Ser Met Asn Pro Ala Arg Ser Phe Gly Pro Ala Val
            180                 185                 190

GTC ATG AAC CGG TTC AGC CCC TCT CAC TGG GTC TTC TGG GTA GGG CCT         739
Val Met Asn Arg Phe Ser Pro Ser His Trp Val Phe Trp Val Gly Pro
195                 200                 205                 210

ATT GTG GGG GCC ATG CTG GCG GCC ATC CTC TAT TTC TAC CTG CTC TTC         787
Ile Val Gly Ala Met Leu Ala Ala Ile Leu Tyr Phe Tyr Leu Leu Phe
            215                 220                 225

CCC TCC TCT CTG AGC CTC CAT GAT CGC GTG GCT GTC GTC AAA GGC ACA         835
Pro Ser Ser Leu Ser Leu His Asp Arg Val Ala Val Val Lys Gly Thr
            230                 235                 240

TAT GAG CCG GAG GAG GAC TGG GAA GAT CAT CGA GAG GAG AGG AAG AAG         883
Tyr Glu Pro Glu Glu Asp Trp Glu Asp His Arg Glu Glu Arg Lys Lys
            245                 250                 255

ACC ATC GAG CTG ACG GCA CAC TGACTGGTGC CGGACAGGGG CCAGTCCCTC            934
Thr Ile Glu Leu Thr Ala His
            260                 265

AGCCCCTGGA CCACTGGAGA AAAGGAAGAC GAAGAGTTTG AAGCACCCCT CCCCAACATC        994

CTCTCAGCTG GGAAGAGGC ATTGGATCCC CATGCTGCTG CACAGGGACA GGAGCAGAAG        1054

CCCATAATGG GACACTTGGG TGTGGGCCAA GGGCTGGAGT CTGACAGGGT CAGGGACATA       1114

GCCGCTTTGG AATCAGGCAG AATGTCTGCC ACAGCTCAGA CCTCAGAGAT TCGTGAATGC       1174

GGTGCCAAGC TCACAGGCGG TCCAGGACCA CACCAGAAAG GGACGACAGC TTGCTTATCT       1234

CTCCCAACCC AGTATCTCAA GTGCCAAAGC CGGCCCCCAG GTGGACAGAG GGACATTTC       1294

CCCCAGAGCT CTTCAGGAGA GGGATAGATG GCTCACGGAG TGCTATTTTA TTTATTTCTG       1354

GTCAAGGATG GGGGTGGGGT GGGGCTGCTG GTGTTTGAGC TGGCGCTTCC CAATAAACCA       1414

CCTATCTTCA AAAAAAAAAA AAAAAAA                                          1442
```

( 2 ) INFORMATION FOR SEQ ID NO:19:

( i ) SEQUENCE CHARACTERISTICS:
        ( A ) LENGTH: 265 amino acids
        ( B ) TYPE: amino acid
        ( D ) TOPOLOGY: linear (ii) MOLECULE TYPE: protein (xi) SEQUENCE DESCRIPTION: SEQ ID NO:19:

```
Met Lys Lys Glu Val Cys Ser Leu Ala Phe Phe Lys Ala Val Phe Ala
 1               5                  10                  15
Glu Phe Leu Ala Thr Leu Ile Phe Val Phe Phe Gly Leu Gly Ser Ala
                20                  25                  30
Leu Lys Trp Pro Ser Ala Leu Pro Thr Ile Leu Gln Ile Ser Ile Ala
            35                  40                  45
Phe Gly Leu Ala Ile Gly Thr Leu Ala Gln Ala Leu Gly Pro Val Ser
        50                  55                  60
Gly Gly His Ile Asn Pro Ala Ile Thr Leu Ala Leu Leu Ile Gly Asn
 65                 70                  75                  80
Gln Ile Ser Leu Leu Arg Ala Val Phe Tyr Val Ala Ala Gln Leu Val
                85                  90                  95
Gly Ala Ile Ala Gly Ala Gly Ile Leu Tyr Trp Leu Ala Pro Leu Asn
            100                 105                 110
Ala Arg Gly Asn Leu Ala Val Asn Ala Leu Asn Asn Asn Thr Thr Pro
        115                 120                 125
Gly Lys Ala Met Val Val Glu Leu Ile Leu Thr Phe Gln Leu Ala Leu
    130                 135                 140
Cys Ile Phe Ser Ser Thr Asp Ser Arg Arg Thr Ser Pro Val Gly Ser
145                 150                 155                 160
Pro Ala Leu Ser Ile Gly Leu Ser Val Thr Leu Gly His Leu Val Gly
                165                 170                 175
Ile Tyr Phe Thr Gly Cys Ser Met Asn Pro Ala Arg Ser Phe Gly Pro
            180                 185                 190
Ala Val Val Met Asn Arg Phe Ser Pro Ser His Trp Val Phe Trp Val
        195                 200                 205
Gly Pro Ile Val Gly Ala Met Leu Ala Ala Ile Leu Tyr Phe Tyr Leu
    210                 215                 220
Leu Phe Pro Ser Ser Leu Ser Leu His Asp Arg Val Ala Val Val Lys
225                 230                 235                 240
Gly Thr Tyr Glu Pro Glu Glu Asp Trp Glu Asp His Arg Glu Glu Arg
                245                 250                 255
Lys Lys Thr Ile Glu Leu Thr Ala His
            260                 265
```

“ISOLATION, CLONING AND EXPRESSION OF TRANSMEMBRANE WATER CHANNEL AQUAPORIN 5 (AQP5)

This application is a continuation-in-part of U.S. application Ser. No. 07/930,168, filed Aug. 17, 1992, (now abandoned) which is in turn a continuation-in-part of application Ser. No. 07/806,273, filed Dec. 13, 1991, now abandoned. The text of these applications is incorporated herein by reference in their entirety.

This invention was made with government support. The U.S. Government may retain certain rights in this invention.

FIELD OF THE INVENTION

The invention relates to $M_r$ 28,000 transmembrane water channel proteins. In particular, the invention relates to the isolation, cloning and expression of transmembrane water channel proteins Aquaporin 1 and Aquaporin 5. The invention further relates to methods for detecting the presence of these Aquaporins in tissue and the preparation of pharmacological agonists and antagonists of the membrane channel proteins for use as therapeutic agents.

BACKGROUND OF THE INVENTION

Cell membranes regulate the passage of materials into and out of a cell, a function which makes it possible to maintain the structural and functional integrity of the cell. It has long been recognized that the basic structure of cell membranes consist of a lipid bilayer having proteins embedded throughout. Proteins contribute to the structural strength of the membrane, act as enzymes to promote chemical reactions, act as carriers for the transport of substances through the membrane and provide breaks in the lipid bilayer so as to form pores through the membrane. Membranes of various cell types differ in biological function largely due to the different kinds of proteins embedded in the lipid bilayer.

Proteins may be embedded in the outer (exofacial) surface of the lipid bilayer, or in the inner (endofacial) surface of the lipid bilayer. Other proteins pass through the lipid bilayer and are exposed on both the inner (i.e., intracellular or cytoplasmic) surface and the outer (i.e., extracellular) surface of the membrane. Still other proteins are more loosely bound to one surface of the membrane or both, depending on the membrane. A number of protein enzymes are either dissolved in the cell membrane or are adherent to it. Many of these enzymes are present on the intracellular surface of the membrane and function at the boundary between the inner surface of the membrane and the cytoplasm to catalyze chemical reactions.

Proteins which penetrate the lipid bilayer, extending all the way through the membrane from one surface to the other, may provide direct watery passages through the interstices of the protein molecules. Such proteins act as carriers, ferrying molecules through the membrane.

Some proteins, as well as some lipids, have carbohydrates attached to their extracellular surface. The carbohydrates may be involved in the recognition and adhesion processes between, for example, cells and cells, cells and antibodies, and cells and viruses.

The human erythrocyte membrane is an accessible, pure membrane source which has provided much information upon which general understandings of membrane structure are based. The erythrocyte membrane is composed of membrane proteins which penetrate the lipid bilayer and a complex of cytoskeletal proteins known as the "membrane skeleton". Integral membrane proteins, which penetrate the lipid bilayer, are known to play roles in transport and structure. The membrane skeleton, which is located just below the intracellular surface of the lipid bilayer, provides shape and reversible deformability of the erythrocyte.

Some protein linkages between the membrane skeleton and the lipid bilayer have been identified. Ankyrin is well understood to provide major linkage between spectrin in the membrane skeleton and a site on the intracellular surface, i.e., the cytoplasmic domain, of the anion transporter channel protein (Bennett et al., 1979, *Nature* 280:468–473; Hargreaves et al., 1980, *J. Biol. Chem.* 255:11965–11972; Tyler et al., 1980 *J. Biol. Chem.* 255:7034–7039).

Other skeleton to bilayer linkages have been identified but are less well understood. Glycophorin C is associated with the membrane skeleton protein 4.1, but the specific linkage remains to be elucidated (Reid et al., 1987, *Blood* 69:1068–1072). Glycophorin A has been shown to relay stimuli from the extracellular surface of the membrane to the membrane skeleton (Anderson et al., 1981, *Nature* 292:158–160; Chasis et al., 1985, *J. Clin. Invest.* 75:1919–1926). Protein 4.1 has been shown to associate with the cytoplasmic domains of glycophorin A (Anderson et al., 1984, *Nature* 307:655–658; Anderson et al., 1985, *Nature* 318:295–298), the anion transporter (Pasternack et al., 1985, J. Biol. Chem. 260:3676–3683) and phosphatidylserine in the lipid bilayer (Cohen et al., 1988, *Biochemistry* 27:617–619; Ribicki et al., 1984, *Blood* 64:30, abstr.). The Rh polypeptide is an integral membrane protein which was found to be associated with the membrane skeleton (Gahmberg et al., 1984, *J. Immunol.* 133:334–337; Ridgwell et al., 1984, *FEBS Lett.* 174:7–10). It has been shown that the Rh protein can be extracted from membrane skeletons with high detergent concentrations (Bloy et al., 1987, *Blood* 69:1491–1497) and lacks an identifiable cytoplasmic domain (Agre et al., 1987, *J. Biol. Chem.* 262:17497–17503). The lack of a cytoplasmic domain suggests that the Rh polypeptide linkage with the membrane skeleton results from a side-by-side association with another skeleton-linked integral membrane protein. Various erythrocyte integral protein blood group antigens have also been identified (Rosse et al., 1989, In: *Red Blood Cell Membranes* (Agre et al., eds.) pp. 299–3234, Marcel Dekker Inc., New York).

It is known that mammalian red cell plasma membranes contain a water-selective channel which confers the cells with the ability to rapidly swell or shrink in response to small changes in extracellular osmolality (Macey (1984) *Amer. J. Physiol.* 246:C195–C203; Solomon et al., 1984, *Ann. N. Y. Acad. Sci.* 414:79–124), and the physiological behavior of the water channel has been extensively studied. Red cell water channels are constitutively active but can be inhibited by submillimolar concentrations of mercural compounds, such as $HgCl_2$. It has been calculated that in the order of 250,000 water channels exist in each red cell (Solomon et al., 1984, *Ann. N.Y. Acad. Sci.* 414: 79–124 ), and red cell water channels are physiologically very similar to the water channel identified in proximal convoluted renal tubules.

Production of Saliva and Tears

The molecular pathways through which salivary and lacrimal glands secrete water are not yet explained (reviewed by Nauntofte, 1992, *Am. J. Physiol.*, 263:G823–G837), and none of the known members of the Aquaporin family exist at these locations nor in large airway epithelium (Nielsen et al, 1993b, *Proc. Natl. Acad. Sci. U.S.A.*, 90:7275–7279 Li et al., 1994, *Pflügers Arch*, in press). Therefore, other Aquaporins may be involved in several important clinical settings. For example, patients with Sjögren's syndrome suffer from the lack of normal tear and saliva secretion due to autoimmune destruction of lacrimal and salivary glands, yet the target antigen in the glandular epithelia is not known (Fox and Saito, 1994, *Arthritis Rheum.*, 37:771–772). Although patients with head and neck cancer may be cured of their malignancies, they often suffer from inanition and aspiration pneumonias due to the inability to secrete saliva after local radiotherapy (Vokes et al., 1993, *N. Engl. J. Med.*, 328:184–194). Dryness of eyes is a common and unexplained aging phenomenon which can lead to loss of vision in some individuals (Greiner and Kenyon, 1994, in *Principles and Practice of Ophthalmology-Basic Sciences*, Albert, et al., eds) Chap. 52, W. B. Saunders Co., Philadelphia, Pa.). Evaporation of water from the large airways is thought to precipitate asthma (McFadden and Gilbert, 1994, *N. Engl. J. Med.*, 330:1362–1367).

In view of the importance of the production (or lack thereof) of saliva, pulmonary secretions, or tears, as described above, therapeutic intervention to restore the ability to produce these secretions is an important goal. However, because the mechanism by which saliva, pulmonary secretions, and tears are produced is not known, such intervention is not currently possible. Thus, a need exists for a system in which the production of tears, pulmonary secretions, and/or saliva can be studied, and ultimately a need exists for therapeutic agents to initiate or enhance secretion.

Neither the DNA sequence nor the amino acid sequence of the water channel protein has previously been determined. Knowledge of the DNA sequence and protein function would provide the art with a means of developing reagents specifically targeted to enhance or inhibit protein function. Such agents would be both diagnostically and therapeutically useful.

SUMMARY OF THE INVENTION

It is an object of the invention to provide a purified $M_r$ 28,000 transmembrane water channel protein and artificial membrane containing it.

It is an object of the invention to provide a purified transmembrane water channel protein encoded by the Aquaporin-1 (AQP1) and/or Aquaporin-5 (AQP5) gene as well as an artificial membrane containing it.

It is also an object of the invention to provide a nucleotide sequence encoding the AQP1 or AQP5 protein, as well as vectors containing the nucleotide sequence, particularly vectors capable of directing expression of the protein in mammalian cells.

It is a further object of the invention to provide a method of determining the tissue distribution and/or prevalence of the AQP1 and AQP5 water channel proteins using, for example, immunoblot analysis or immunohistochemical staining with antibodies specific for this water channel protein or alternatively in situ hybridization.

Still another object of the invention is to provide a method for identifying therapeutic agents useful as agonists or antagonists of the membrane water channel.

These and other objects of the invention are provided by one or more of the following embodiments of the invention.

In one embodiment, a cDNA sequence is provided which encodes for a water channel protein corresponding to the amino acid sequence of AQP1 or AQP5. A biologically functional plasmid or viral DNA is also provided which includes a DNA sequence encoding the water channel protein.

In another embodiment, a method of producing the water channel protein is presented which comprises obtaining a host cell transformed with an expression vector containing an intron-free DNA sequence encoding the water channel protein, growing the host cell to express the water channel protein, and recovering a preparation of the water channel protein. Transformed or transfected host cells, as well as recombinantly produced protein, are also contemplated by the invention.

Synthetically produced liposomes which contain the water channel protein described herein also form part of the invention.

Still another embodiment of the invention is directed to a rapid and reliable method of screening potentially useful pharmacological agonists or antagonists of the water channel. The method comprises testing potential agents by adding the agent to be tested to AQP-containing proteoliposomes or to red cell membrane vesicles (which contain AQP proteins) and measuring augmentation or inhibition of osmotic water permeability after exposure to buffers with increased or decreased osmotic strength.

Yet another embodiment of the invention is directed to therapeutic agents useful as agonists or antagonists and methods of treating certain disease states with such agents.

It has been discovered that a $M_r$ 28,000 protein functions as a molecular water channel. The invention described herein provides the art with the nucleotide sequence of proteins which function as water channels in a variety of tissues. The cDNA sequence of the $M_r$ 28,000 protein AQP1 has now been determined and found to be capable of expression in heterologous biological systems, as taught herein. Knowledge of the cDNA sequence of this protein enables the development of therapeutic and diagnostic reagents which are useful in the diagnosis and treatment of certain disease states.

The inventors have also isolated and characterized the fifth mammalian member of the Aquaporin family which is expressed at locations implicating it in the generation of saliva, tears, and pulmonary secretions. Since the molecular pathway by which water is secreted by salivary glands is unknown, a cDNA was isolated from rat submandibular gland by homology cloning. Similar to other Aquaporins, the salivary cDNA encodes a 265-residue polypeptide with six putative transmembrane domains separated by five connecting loops (A–E); a mercurial-inhibition site in extracellular loop E, and a cAMP-protein kinase phosphorylation consensus site in cytoplasmic loop D. In vitro translation yielded a 27-kDa polypeptide, and expression of the cRNA in Xenopus oocytes conferred a 20-fold increase in osmotic water permeability ($P_f$) which was reversibly inhibited by 1 mM $HgCl_2$. Northern analysis demonstrated a 1.6-kilobase mRNA in submandibular, parotid, and sublingual salivary glands, lacrimal gland, eye, trachea, and lung. In situ hybridization revealed a strong hybridization over the corneal epithelium in eye and over the secretory lobules in salivary glands. These studies have identified a new mammalian member of the Aquaporin water channel family (gene symbol AQP5) which is implicated in the generation of saliva, tears, and pulmonary secretions.

The invention described herein provides the art with the nucleotide sequence of a protein which functions as a water channel in salivary and lacrimal glands and in lung tissues. The cDNA sequence of this 27 kDa protein has now been determined and found to be capable of expression in heterologous biological systems, as taught herein. Knowledge of the cDNA sequence of this protein enables the development of diagnostic and therapeutic reagents which are useful in the diagnosis and treatment of certain symptomatic and disease states.

BRIEF DESCRIPTION OF THE DRAWINGS

FIG. 2 shows the nucleotide and deduced amino acid sequences of AQP1 SEQ ID NO:16.

FIG. 15 shows osmotic water permeability ($P_f$) of oocytes injected with 50 nl of water without RNA or oocytes injected with 5 ng of the indicated cRNAs.

DETAILED DESCRIPTION OF THE INVENTION

Figure 1:
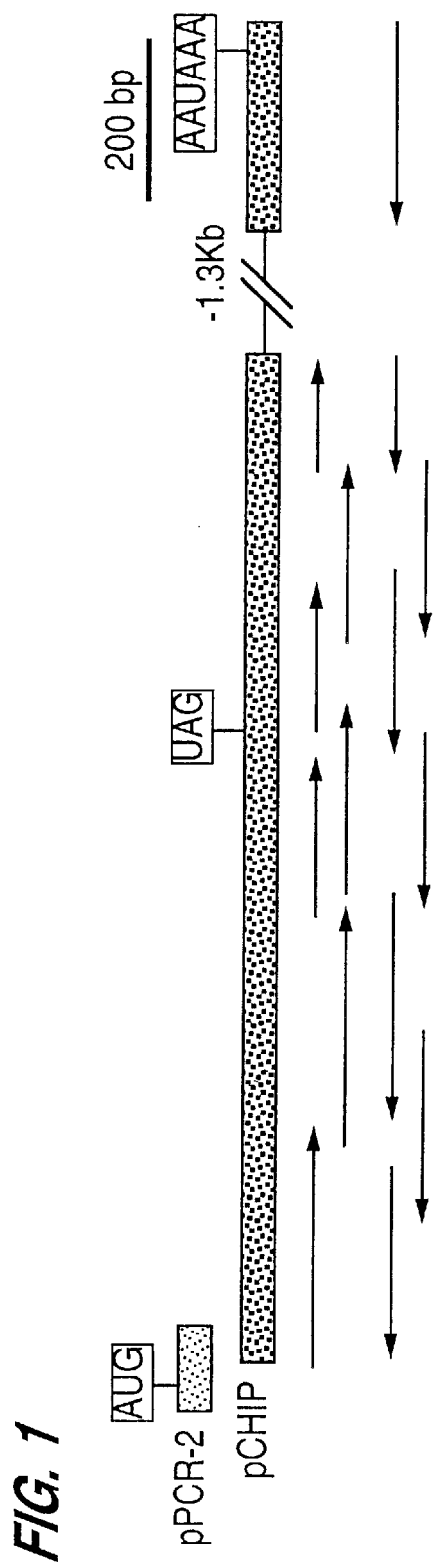
FIG. 1 shows the organization of AQP1 recombinants.

Using a Xenopus oocyte swelling assay, it has been demonstrated that red cell and renal tubule water channels are protein structures encoded by a mRNA of approximately 2.5 kb (Zhang et al., 1990, *J. Biol. Chem.* 265:15375–15378; Zhang et al., 1991, *J. Clin. Invest.* 88:1553–1558). Target analysis using radiation inactivation has revealed the functional unit of the proximal tubule water channel is a protein of approximately $M_r$, 30 kDa (van Hoek et al., 1991, *J. Biol. Chem.* 266:16633–16635). Although both the anion exchanger-band 3 (Solomon et al., 1984, *Ann. N.Y. Acad. Sci.* 414: 79–124) and the glucose transporter (Fischbarg et al., 1990 *Proc. Natl. Acad. Sci. USA* 87:3244–3247) have been purported to produce increased membrane water permeability, recent studies have demonstrated that neither is the well-defined water channel (Zhang et al., 1991, *J. Clin. Invest.* 88:1553–1558).

Denker et al. (*J. Biol. Chem.*, 1988, 263:15634–15642) described the isolation and partial characterization of an abundant $M_r$, 28,000 erythrocyte integral (transmembrane) protein linked to the membrane skeleton. This protein was found to exist in two forms, "28kDa" and "gly28kDa", the extracellular domain of the latter containing N-glycosylation. Affinity purified rabbit polyclonal anti-28kDa quantitatively immunoprecipated 28kDa and gly28kDa. Quantitative immunoprecipitation indicated that each erythrocyte contains 120,000 to 200,000 copies of this protein. Anti-28kDa immunoblots of several nonerythroid tissues showed that only kidney displayed immunoreactive 28kDa. Immunohistochemical staining of human kidney with anti-28kDa demonstrated prominent staining over the apical brush borders of proximal convoluted tubules.

The $NH_2$-terminal amino acid sequence of the first 35 residues of purified 28kDa was initially determined. This sequence was analyzed by computer for homology with known amino acid sequences. A single significant homology was found with a 26kDa major intrinsic protein (MIP) from bovine lens (Gorin et al., 1984, *Cell* 39:49–59). When the $NH_2$ termini of the 28kDa protein and MIP are aligned, 13 of the 35 amino acids were found to be identical. Such significant homologies are known to exist between other membrane proteins of erythrocytes and lens fiber cells (Allen et al., 1987, *Biochem. Biophys. Res. Commun.* 149:266–275). The existence of such homologies may be related to specialized features common to both of these cell types. Common features of erythrocytes and differentiated lens fiber cells include lack of nuclei and intracellular organelles, both cell types being essentially membrane sacks which contain cytoplasm composed nearly entirely of uniform species of protein (hemoglobin and crystallins, respectively). While similarities exist between the two proteins, such similarities including similar size, a cytoplasmic COOH-terminal domain, peculiar detergent solubilities and the ability to form multiunit transmembrane oligomers, 28kDa and MIP are not likely to be species variants of the same protein, since they are only 37% identical. Furthermore, immunoblots of rat lens membranes failed to react with anti-28kDa, whereas Denker et al. (*J. Biol. Chem.*, 1988, 263:15634–15642) observed strong reactions of rat erythrocyte and kidney membranes.

A cDNA for 28kDa has now been isolated, cloned and expressed. Since 28kDa has been found to share homology with all known members of the MIP channel family, this protein was originally designated "CHIP28" for channel-like integral membrane protein of 28kDa. Hereinafter the 28kDa protein, and gene sequences encoding it, will be referred to as Aquaporin-1 or AQP1.

FIG. 2 shows the 5' untranslated nucleotide sequence, the open reading frame, the first 500 bp of the 3' untranslated sequence, and the 269 amino acid sequence of AQP1, and the terminal 3' untranslated nucleotide sequence.

Whereas a particular nucleotide sequence is disclosed herein, other sequences which encode for AQP1 are also encompassed by the invention, i.e., different DNA sequences encoding the same amino acid sequence. In addition, the cDNA molecule described herein need not be complete in order to be useful, so long as the protein encoded thereby retains the ability to form a water channel.

Other Members of the Aquaporin Family

Surprisingly, no clinical phenotype was observed in humans homozygous for Aquaporin-1 knockout mutations, suggesting that other water channels must exist (Preston et al., 1994a, *Science*, 265:1585–1587). The sequences of AQP1 (Preston and Agre, 1991) and the functionally undefined homolog MIP, major intrinsic protein of lens (Gorin et al., 1984, Cell, 39:49–59), have led to homology cloning of other members of the Aquaporin family (reviewed by Knepper, 1994, Proc. Natl. Acad. Sci. U.S.A., 91:6255–6258). AQP-CD is a water channel protein expressed in renal collecting ducts and is encoded by Aquaporin-2 (Fushimi et al, 1993, Nature, 361:549–552.; Sasaki et al, 1994, J. Clin. Invest., 93:1250–1256). Antidiuretic hormone regulates the subcellular distribution of this protein (Nielsen et al, 1993c, J. Cell Biol., 120:371–383; DiGiovanni et al, 1994, Proc. Natl. Acad. Sci. U.S.A., 91:8984–8988), and Aquaporin-2 is the site of mutations in some forms of nephrogenic diabetes insipidus (Deen et al, 1994, Science, 264:92–95). Aquaporin-3 encodes a water channel protein which is also permeable to glycerol and is located in the basolateral membranes of renal medullary collecting duct and intestine (Ishibashi et al, 1994, Proc. Natl. Acad. Sci. U.S.A., 91:6269–6273). A mercury-insensitive water channel was identified (Hasegawa et al., 1994, Biol. Chem., 269:5497–5500), and Aquaporin-4 is most abundantly expressed in brain where it has been implicated as the hypothalamic osmoreceptor which mediates vasopressin secretion (Jung et al., 1994a, Proc. Natl. Acad. Sci. U.S.A., 91:13052–13056).

Since the molecular pathway by which water is secreted by salivary glands is unknown, a cDNA was isolated from rat submandibular gland by homology cloning, using primers based on the most conserved sequences of the Aquaporin family. A nucleotide probe and subsequently a cDNA of 1.5 kilobases (kb) was cloned from a salivary gland cDNA library. The cDNA contained a 795 base pair (bp) open reading frame which encoded a protein of the Aquaporin family.

Similar to other Aquaporins, the salivary cDNA encodes a 265-residue polypeptide with six putative transmembrane domains separated by five connecting loops (A–E); the $NH_2$— and COOH-terminal halves of the polypeptide are sequence-related, and each contains the motif Asn-Pro-Ala. A mercurial-inhibition site is present in extracellular loop E, and cytoplasmic loop D contains a cAMP-protein kinase phosphorylation consensus.

Using a Xenopus oocyte swelling assay, it has been demonstrated that the protein encoded by the 1.5 kb Aquaporin 5 cDNA is a water channel protein, similar to the red cell and renal tubule water channels which are protein structures encoded by a mRNA of approximately 2.5 kb (Zhang et al., 1990, J. Biol. Chem. 265:15375–15378; Zhang et a., 1991, J. Clin. Invest. 88:1553–1558). In vitro translation yielded a 27-kDa polypeptide, and expression of the cRNA in Xenopus oocytes conferred a 20-fold increase in osmotic water permeability ($P_f$) which was reversibly inhibited by 1 mM $H_gCl_2$. Northern analysis demonstrated a 1.6-kilobase mRNA in submandibular, parotid, and sublingual salivary glands, lacrimal gland, eye, trachea, and lung. In situ hybridization revealed a strong hybridization over the corneal epithelium in eye and over the secretory lobules in salivary glands. These studies have identified a new mammalian member of the Aquaporin water channel family (gene symbol AQP5) which is implicated in the generation of saliva, tears, and pulmonary secretions.

Whereas a particular nucleotide sequence is disclosed herein, other sequences which encode for Aquaporin-5 are also encompassed by the invention, i.e., different DNA sequences encoding the same amino acid sequence. In addition, the cDNA molecule described herein need not be complete in order to be useful, so long as the protein encoded thereby retains the ability to form a water channel or to bind to antibodies specific for AQP5.

Proteins encoded by the nucleotide sequence of the invention, as well as proteins which correspond to the AQP1 protein or the AQP5 protein, i.e., proteins containing conservative amino acid substitutes, are also encompassed by the invention. Conservative amino acid substitutions are substitutions of one amino acid residue in a sequence by another residue of similar properties, such that the secondary and tertiary structure of the resulting peptides are substantially the same. Amino acids which maybe conservatively substituted for one another are well known to those of ordinary skill in the art. Proteins of this invention comprising conservative amino acid substitutions retain the ability to form a water channel. The sequence of proteins which correspond to AQP1 or AQP5 will usually be 75% identical with the sequence of AQP1 or AQP5, respectively, preferably 85% identical and most preferably 90% identical.

The recombinantly produced proteins of this invention are optionally substantially pure, being free from all other human proteins. The protein may be obtained by growing transformed cells in culture under conditions wherein the cloned DNA of the invention is expressed.

The practice of the invention employs, unless otherwise indicated, conventional molecular biology, microbiology and recombinant DNA techniques within the skill of the art. Such techniques are explained fully in the literature. See, e.g., Sambrook et al., 1989, Molecular Cloning: A Laboratory Manual, Cold Spring Harbor Labs, Cold Spring Harbor, N.Y., 2nd Ed.; DNA Cloning: A Practical Approach, Volume I and II (Glover, ed., 1985); Oligonucleotide Synthesis (Gait, ed., 1984); Nucleic Acid Hybridization (Hames & Higgins, eds., 1985); Transcription and Translation (Hames & Higgins, eds. 1984); Animal Cell Culture (Freshney, ed., 1986); and Perbal, 1984, A Practical Guide to Molecular Cloning.

The AQP Nucleotide Sequence

The DNA sequence encoding AQP1 or AQP5 can be synthesized chemically or isolated by one of several approaches. The complete sequence may be assembled from overlapping oligonucleotides prepared by standard methods and assembled into a complete coding sequence.

See, e.g., Edge (1981) Nature 292:756; Nambair, et al. (1984) Science 223:1299; Jay, et al. (1984) J. Biol. Chem., 259:6311. The isolation methods will rely in part on nucleic acid hybridization using appropriate single stranded or double stranded nucleotide or oligonucleotide probes. Such probes can be constructed synthetically, based on the DNA or amino acid sequences disclosed herein, or isolated from genomic or cDNA clones also described herein.

The basic strategies for preparing oligonucleotide probes and DNA libraries, as well as their screening by nucleic acid hybridization, are well known to those of ordinary skill in the art. See, e.g., Sambrook, et al., "Molecular Cloning: a Laboratory Manual" (1989); B. Perbal, "A Practical Guide To Molecular Cloning" (1984). First, a DNA library is prepared. The library can consist of a genomic DNA library from a human source. Human genomic libraries are known in the art. More preferred are DNA libraries constructed of cDNA, prepared from poly-A-plus RNA (mRNA) by reverse transcription. The mRNA is isolated from a tissue believed to express the protein cross-reactive with AQP1 or AQP5. A suitable source of mRNA for cDNA library constructions expected to contain AQP5 is salivary glands, lacrimal glands cornea or lung tissue. The genomic DNA or cDNA is cloned into a vector suitable for construction of a library. The construction of an appropriate library is within the skill of the art. See, e.g., B. Perbal, supra. Once the library is constructed, oligonucleotides are used to probe the library to identify the segment carrying a sequence encoding AQP1 or AQP5.

Nucleic Acid Probes

Oligonucleotides can be designed and produced for use as hybridization probes to locate the other coding sequences. In general, the probes are synthesized chemically, preferably based upon known nucleic acid sequences, such as the sequences shown in FIG. 2 or FIG. 14A. Ultimately, the isolated segments of DNA are ligated together in such a way that the correct mature protein is encoded.

Nucleotide sequences are selected so as to correspond to codons encoding the amino acid sequence. Since the genetic code is redundant, degenerate probes include several oligonucleotides to cover all, or a reasonable number, of the possible nucleotide sequences which encode a particular amino acid sequence. Thus, it is generally preferred, in selecting a region of the sequence upon which to base degenerate probes, that the region not contain amino acids whose codons are highly degenerate. It may not be necessary, however, to prepare probes containing codons whose usage is rare in the animal from which the library was prepared. Alternative methods using a long probe (greater than 35 bp) which is not degenerate may also be used as described by Lathe, R. (1985), J. Mol. Biol., 183:1–12 (discussed in Sambrook, et al.). One of skill in the art may find it desirable to prepare probes that are fairly long and/or encompass regions of the amino acid sequence which would have a high degree of redundancy in the corresponding nucleic acid sequences. In other case of probes simultaneously, each to sets of probes simultaneously, each to a different region of the gene. While the exact length of any probe employed is not critical, typical probe sequences are no greater than 1000 nucleotides in length, more typically they are not greater than 500 nucleotides, even more typically they are no greater than 250 nucleotides; they may be no greater than 100 nucleotides, and also may be no greater than 75 nucleotides in length. Generally it is recognized in the art that probes from about 14 to about 20 base pairs are usually effective. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Procedures for construction and expression of mutant proteins of defined sequence are well known in the art. A DNA sequence encoding a mutant form of AQP1 or AQP5 can be synthesized chemically or prepared from the wild-type sequence by one of several approaches, including primer extension, linker insertion and PCR (see, e.g., Sambrook, et al.). Mutants can be prepared by these techniques having additions, deletions and substitutions in the wild-type sequence. It is preferable to test the mutants to confirm that they are the desired sequence by sequence analysis and/or the assays described below. Mutant protein for testing may be prepared by placing the coding sequence for the polypeptide in a vector under the control of a promoter, so that the DNA sequence is transcribed into RNA and translated into protein in a host cell transformed by this (expression) vector. The mutant protein may be produced by growing host cells transfected by an expression vector containing the coding sequence for the mutant under conditions whereby the polypeptide is expressed. The selection of the appropriate growth conditions is within the skill of the art.

Producing the Recombinant Peptide

Preferably, DNA from the selected clones should be subcloned into an expression vector, and the protein expressed by cells transformed with the vector should be tested for immunoreactivity with antibodies against the recombinant protein of this invention prepared as described below. Such subcloning is easily within the skill of the ordinary worker in the art in view of the present disclosure. The amino acid coding region of the DNA sequence of this invention may be longer or shorter than the coding region of the deposited vectors, so long as the recombinant peptide expressed by the DNA sequence retains at least one epitope cross-reactive with antibodies which are specifically immunoreactive with AQP1 or AQP5. The preparation of selected clones which contain DNA sequences corresponding to all or part of the sequence of AQP5 may be accomplished by those of ordinary skill in the art using conventional molecular biology techniques along with the information provided in this specification.

The expression products of DNA sequences of the present invention may be produced using a wide variety of host/vector combinations. A vector is a replicon, such as a plasmid, phage or cosmid, to which another DNA segment may be attached so as to bring about the replication of the attached segment. For example, useful vectors may comprise segments of chromosomal DNA, non-chromosomal DNA (such as various known derivatives of SV40 and known bacterial plasmids, e.g., plasmids from E. coli including colE1, pcR1, pBR322, pMB9 and RP4), or synthetic DNA sequences, phage DNAs (M13) including derivatives of phage (e.g., NM 989), vectors useful in yeasts, vectors useful in eukaryotic cells (such as vectors useful in animal cells, e.g., those containing SV40 adenovirus and retrovirus derived DNA sequences) and vectors derived from combinations of plasmids and phage DNAs (such as plasmids which have been modified to employ phage DNA), or other derivatives thereof.

Expression vectors according to this invention are also characterized by at least one expression control sequence that may be operatively linked to the coding sequence of the Aquaporin protein, inserted in the vector to control and regulate the expression of the cloned DNA sequence. Useful expression control sequences are well known in the art. Examples of useful expression control sequences are the lac system, the trp system, the tac system, the trc system, major operator and promoter regions of phage lambda ($\lambda$), the control region of fd coat protein, the glycolytic promoters of yeast (e.g., the promoter for 3-phosphoglycerate kinase), the promoters of yeast acid phosphatase (e.g., Pho5), the promoters of the yeast alpha ($\alpha$)-mating factors and promoters derived form polyoma, adenovirus, retrovirus, or simian virus (e.g., the early and late promoters of SV40), and other sequences known to control the expression of genes of prokaryotic or eukaryotic cells and their viruses or combinations thereof.

Furthermore, within each specific expression vector, various sites may be selected for insertion of the DNA sequences of this invention. These sites are well recognized by those of skill in the art and they are usually designated by restriction endonucleases. It is, of course, to be understood that an expression vector useful in this invention need not have a restriction endonuclease site for insertion of the chosen DNA fragment. Instead, the vector can be joined to the fragment by alternative means. The expression vector, and in particular the site chosen therein for insertion of a selected DNA fragment and its operative linking therein to an expression control sequence, is determined by a variety of factors, e.g., number of sites susceptible to a particular restriction enzyme, contamination or binding of the protein to be expressed by host cell proteins difficult to remove during purification, and expression characteristics, such as the location of start and stop codons relative to the vector. An insertion site for a DNA sequence is determined by a balance of these factors, not all selections being equally effective for a given case.

Useful expression hosts include well known prokaryotic and eukaryotic hosts, including E. coli, such as E. coli SG-936, E. coli HB 101, E. coli w3110, E. coli X1776, E. coli X 2282, E. coli DHI, and E. coli MRC1, Pseudomonas, Bacillus, such as Bacillus subtilis, Streptomyces, yeasts and other fungi, COS cells, CHO cells, human cells and plant cells in tissue culture. Of course, not all host/expression vector combinations function with equal efficiency in expressing the DNA sequences of this invention or in producing the protein of this invention. However, a particular selection of a host/expression vector combination may be made by those skilled in the art. It is possible to purify a protein cross-reactive with AQP1 or AQP5 from an appropriate tissue/fluid source; however, a cross-reactive protein or polypeptide may also be produced by recombinant methods from a DNA sequence encoding such a protein or polypeptide. Polypeptides corresponding to the recombinant protein of this invention may be obtained by transforming cells with an expression vector containing DNA from a clone selected from an mammalian (preferably human) library as described above. Suitable expression vector and host cell systems are well known to those of ordinary skill in the art, and are taught, for instance, in Sambrook, et al., 1989. The peptide may be obtained by growing the transformed cells in culture under conditions wherein the cloned DNA is expressed. Of course, the peptide expressed by the clone may be longer or shorter than the respective Aquaporin so long as the peptides are immunologically cross-reactive. Preferably, the recombinant proteins will have water channel activity, in addition to immunologic cross-reactivity.

AQP1 has been discovered to be the structural unit of the red blood cell and proximal renal tubule water channel. AQP1 not only exists in RBCs and the proximal renal tubule (where most of the glomerular filtrate is reabsorbed), but also exists in the choroid plexus in the brain, the ciliary body in the anterior chamber of the eye, in the pulmonary and intestinal endothelium, and in the heart. Studies with AQP1 and antibodies has also led to the identification of this protein in salivary glands and sweat glands. The existence of this protein in all of these sites indicates that AQP1 protein is involved in a variety of functions, e.g., the modulation of cellular turgor, secretion of cerebral spinal fluid (by the choroid plexus), aqueous humor (anterior chamber of the eye).

It has been determined that the AQP1 proteins 28kDa and gly28kDa exist as a multisubunit transmembrane oligomer. Hydrodynamic studies indicate that the 28kDa-gly28kDa oligomer is a tetramer containing both 28kDa ($M_r$ 28,000) and gly28kDa ($M_r$ ranging from 35,000 to 60,000) subunits.

Purified AQP1 has also been inserted into synthetic liposomes containing carboxyfluorescein and water permeability of the resulting liposomes measured. It has been discovered that the ability of AQP1 to conduct water does not require the specialized lipid composition or bilayer structure of the RBC.

Knowledge of the DNA sequence of a protein essential for water transport enables the design of drugs specifically targeted for use in therapy. Such drugs include agonist and antagonists of AQP1 or AQP5.

Testing of water channel activity may be performed by injection of oocytes with in vitro synthesized AQP1 or AQP5 RNA or by the development of stably transfected cell lines which may be used in a modification of the $^3H_2O$ uptake assay. The AQP1 protein is not known to be expressed in any cell line, but can be inserted by standard transfection methodologies to create stable cell lines which overexpress the protein. AQP1 constitutes the major water channel of red cell membranes. Therefore red cell membranes and membrane vesicles may also be used in a method similar to the liposome assay described herein to test for potential pharmacological agonists and antagonists.

By using the oocyte-swelling assay, the $^3H_2O$ assay, the protecliposome assay or the red cell membrane assay, or a combination of these assays to measure water permeability, potential pharmacological agents may be screened for specific effects on AQP1 or AQP5 function. Monoclonal antibodies specific for epitopes present on the exofacial loops of AQP1 or AQP5 may be screened for their ability to inhibit water channel activity upon binding. Since organomercurials are known to inhibit water channel activity, reagents with structures related to organomercurials, such as p-chloromercuribenzene sulfonate, are promising inhibitors. The primary sequences of AQP1 and AQP5 provided herein permits the design of specific agonists or antagonists.

Depending on the expression vector chosen, the peptide may be expressed as a fusion protein or a mature protein which is secreted or retained intracellularly, or as an inclusion protein. The desired polypeptides can be recovered from the culture by well-known procedures, such as centrifugation, filtration, extraction, and the like, with or without cell rupture, depending on how the peptide was expressed. The crude aqueous solution or suspension may be enriched for the desired peptide by protein purification techniques well known to those s killed in the art.

Antibody Production

Antibodies which are specifically reactive with the recombinant peptide of this invention may be obtained in a number of ways which will be readily apparent to those skilled in the art (see, e.g., Sanbrook et. al.). The recombinant protein, obtained as described above can be injected into an animal as an immunogen to elicit polyclonal antibody production. The resultant polyclonal antisera may be used directly or may be purified by, for example, affinity absorption using recombinantly produced AQP1 or AQP5 coupled to an insoluble support. Purification of the antibodies can be accomplished by selective binding from the serum, for instance by using cells transformed with an AQP1 or AQP5 DNA sequence.

In another alternative, monoclonal antibodies specifically immunoreactive with the protein may be prepared according to well known methods (See, e.g., Kohler and Milstein, 1976, *Eur. J. Immunol.,* 6:611), using the peptide of this invention as an immunogen, using it for selection or using it for both functions. These and other methods for preparing antibodies that are specifically immunoreactive with the recombinant protein of this invention are easily within the skill of the ordinary worker in the art.

Diagnostic Assays

Detection of proteins cross-reactive with AQP1 or AQP5 and their expression, may be on the nucleotide or peptide level. Antibodies can be prepared by immunizing mammals with peptides expressed from nucleic acid sequences corresponding to cross-reactive polypeptides, as indicated above, and selecting those antibodies specific to the particular Aquaporins using techniques that are well known to those skilled in the art. These antibodies can detect the presence of cross-reactive protein by a variety of immunoassay techniques. The nucleotide probe sequences provided herein can be used to detect expression of mRNA corresponding to cross-reactive proteins in accordance with any of the standard techniques. Expression may be detected either by in situ hybridization or by extraction and detection of mRNA. The particular procedures for gene probe assays and immunoassays are well-known to those skilled in the art.

The AQP1 or AQP5 protein, respectively, may be used in immunoassay procedures to detect autoantibodies as a diagnostic tool for assisting in identification of individuals suffering from autoimmune diseases which involve immune attack on specific water channel proteins. Such diseases include Sjögren syndrome (autoimmune destruction of salivary glands, lacrimal glands, and pulmonary epithelium). AQP5 may be the target antigen driving the autoimmune process in Sjögren syndrome, and development of diagnostic kits may permit definitive diagnosis of this disorder. In a related undesirable immune attack, AQP5 (or AQP1 which resides in corneal endothelium) may be target antigens driving the immune rejection process in corneal transplants. Immunometric assays to detect anti-AQP antibodies may permit definitive diagnosis of this disorder or provide improved tissue compatibility assessment of donor and recipient tissues before surgery.

Alternatively, use of promoter elements driving AQP1 or AQP5 expression may permit identification of pharmacologic agents (such as corticosteroids) which may boost expression of the protein and improve respiratory function in infant respiratory distress syndrome. For example, cultured human epithelial cells can be treated with candidate pharmacologic agents and subsequently the cells can be tested for expression of AQP5 by in situ hybridization as described below in the Examples. This screening procedure will identify agents which have the potential to increase expression of AQP5 in vivo.

Immunoassays

The antibodies of the present invention can be used to detect epitopes found on proteins cross-reactive with AQP1 or AQP5, respectively, in histological sections. In particular, immunohistochemical assays may be used to detect and/or quantify AQP5 in salivary glands and lacrimal glands, as well as other eye tissue and lung tissue.

One can detect antibody binding to tissue sections by any detection means known in the art for example, a radiolabel or a stain. A particularly useful stain employs peroxidase, hydrogen peroxide and a chromogenic substance such as aminoethyl carbazole. The peroxidase (a well known enzyme available from many sources) can be coupled to an anti-AQP antibody or merely complexed via one or more antibodies to an antibody which specifically binds a protein which is cross-reactive with AQP1 or AQP5. For example, a rabbit anti-AQP5 antibody can be visualized with a goat anti-rabbit-IgG when the latter is complexed to peroxidase. Such techniques are well known in the art. Other chromogenic substances and enzymes may also be used. Radiolabeling of antibodies may also be used to detect antibody binding to sections. Labeled antibodies may be anti-AQP5 or second antibodies immunoreactive with anti-AQP5 antibodies. Again, such techniques are well known.

The precise technique by which a protein cross-reactive with the AQP1 or AQP5 gene product is detected in patients is not critical to the invention. Biochemical or immunological techniques can be used which do not employ immunohistochemistry, although that is the preferred method of the present invention. Solution assay methods, including colorimetric, chemiluminescent or fluorescent immunoassays such as ELISA, sandwich and competitive immunoassays, immuno-diffusion, radio immunoassay, immunoelectrophoresis, Western blot and other techniques, may be used to detect and quantitate proteins cross-retactive with a peptide having all or a part of the sequence of FIG. 2 or FIG. 14A in a patient by preparing an extract of a tissue sample from the patient and assaying the extract.

An antibody reactive with the AQP5 gene product can be quantitated in a biological fluid, such as serum, plasma, effusions, ascites, urine, cerebrospinal fluid, semen, breast aspirates and fluids of ovarian origin, using any protein detection means known in the art. Preferred methods employ immunological detection means. These include: radioimmunoassay, enzyme linked immunoadsorbent assay, complement fixation, nephelometric assay, immunodiffusion or immunoelectrophoretic assay and the like. Plasma should be anti-coagulated before use, as is known in the art. Cellular elements and lipid may be removed from fluids, e.g., by centrifugation. For dilute fluids, such as urine, protein may be concentrated, e.g., by ultra-filtration or salting-out. Such assays may detect anti-AQP5 antibodies in the serum of individuals with Sjögren's syndrome.

Nucleotide Probe Assays for Expression

An elevated level of AQP5 mRNA in a cell corresponds to elevated AQP5 protein expression by the cell, and AQP5 mRNA can be quantitated in a number of ways. The nucleic acid probes described above for use in screening gene libraries and selecting clones may also be used to detect mRNA transcripts in cells that express a protein cross-reactive with the AQP5 gene product. These probes preferably correspond to a sequence which encodes portions of the distinct sequences of AQP5 (see FIG. 14A). The probe can be either single or double stranded DNA or RNA. The size of a probe can vary from less than approximately 20 nucleotides to hundreds of nucleotides. The most desirable nucleotide probes do not detect nucleotide sequences unrelated to their intended target, do not show significant homology with unrelated nucleotide sequences, and do not contain complementary sequences such that they would self-hybridize or fold upon themselves. The guanine and cytosine content of desirable probes is not so high as to promote non-specific hybridization with unrelated sequences rich in guanine and cytosine. Finally, the melting temperature and free energy of binding are generally favorably suited to the detection technique for which they are intended. The probe may be radio-labeled, labeled with a fluorescent material, a biotinylated nucleotide, or the like. Procedures for the preparation and labeling of nucleotide probes are well known in the art.

In situ hybridization of nucleotide probes to tissue sections is performed using standard methods, as described by, e.g., Baldino, et al., *Methods in Enzymol.,* 1989, vol. 168, p.

761–77; Emson, et al., *Methods in Enzymol.,* 1989, vol. 168, p. 753–61; Harper, et al., *Methods in Enzymol.,* 1987, vol. 151, p. 539–51; Angerer, et al., *Methods in Enzymol.,* 1987, vol. 152, p. 649–61; Wilcox, et al., *Methods in Enzymol.,* 1986, vol. 124 , p. 510–33, incorporated herein by reference, using nucleotide probes described above. One preferred method for detecting mRNA associated with expression of the cross-reactive protein is in situ hybridization to tissue sections taken from tumors. Detection of hybridization by a probe having a nucleotide sequence corresponding to the amino acid sequence of AQP5 in the cells indicates expression by that cell of MRNA corresponding to a protein cross-reactive with the AQFP5 gene product. Tissue sections are prepared as for immunohistochemistry.

Alternatively, extracts of RNA from tissue samples can be analyzed for the presence of sequences encoding the proteins of this invention. The diagnostic test employing a nucleotide probe will employ a biological sample from an individual. Nucleic acids are recovered from the sample employing standard techniques well known to those skilled in the art. The nucleic acid then is incubated with the probe and hybridization is thereafter detected. The presence of a nucleic acid whose sequence corresponds to that of the probe is preferably detected by Northern blot, or slot/dot blot. Using Northern blotting or dot hybridization, purified RNA samples of known concentration and integrity can be hybridized with labeled AQP5 probes. For each sample, the signal which is obtained can be compared radiometrically to the signal obtained when the same sample is hybridized to a labelled probe for a constitutively expressed gene whose expression does not vary from cell to cell or sample to sample. Comparison of the ratios between different samples permits estimation of the differences in AQP5 levels.

Alternatively, a nucleic acid whose sequence corresponds to the sequence of AQP5 may be detected in the RNA extract of tumor tissue by nucleic acid amplification, using primers corresponding to the nucleic acid sequence of AQP5 (see, e.g., methods reviewed in Van Brunt, Biotechnology, 8:291–294, 1990). Similar primers can be used to amplify genomic DNA sequences encoding AQP5. The preferred method of amplification uses the polymerase chain reaction (PCR). Primers can be constructed corresponding to unique portions of the nucleic acid sequence of AQP5, determined as described above for nucleic acid probes. Using these primers, RNA or DNA in a nucleic acid extract of tumor tissue will be amplified by PCR only if it contains the unique AQP5 sequences.

Alternatively, the level of AQP5 mRNA expression can be estimated by quantitative polymerase chain reaction. Using primers whose sequences correspond to the AQP5 nucleotide sequence, cDNA can be synthesized initially using reverse transcriptase, th en the resultant cDNA amplified according to the polymerase chain reaction. The reaction is run under conditions and terminated so as to produce amounts of amplified products in proportion to the amount of mRNA originally present in the sample. The amount of product can be quantitated by ethidium fluorescence in comparison to known standards following electrophoresis, or by dot hybridization with labeled probes. Expression of constitutively expressed genes can be measured as a control, permitting standardized comparison of results, such as with the previously described hybridization reactions. Treatment of samples with ribonuclease A or other RNAses in control samples prior to amplification verifies that the signal is derived solely from RNA. Similar assays may be done of AQP1 expression.

Therapeutic Applications

Figure 16:
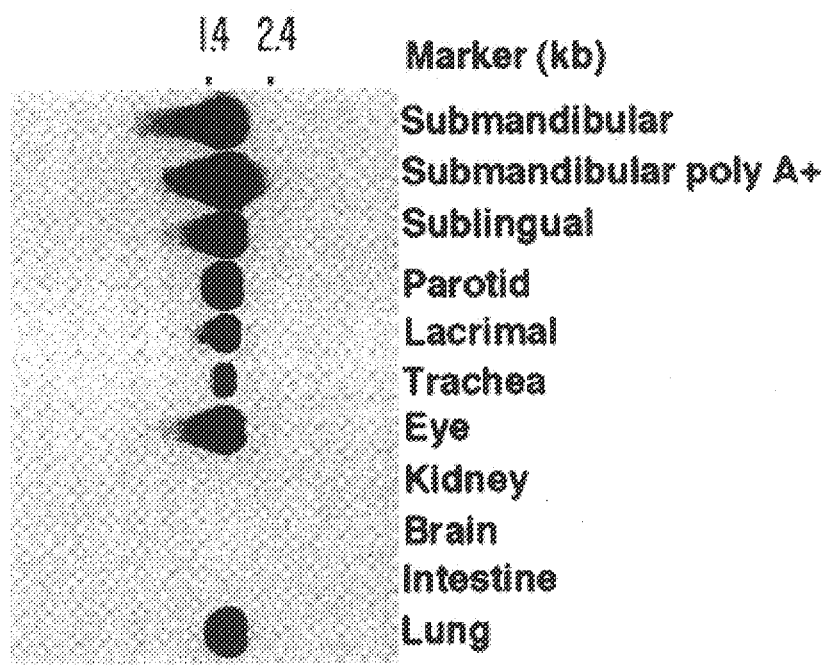
FIG. 16 shows Northern analysis of AQP5 mRNA in rat tissues.

*Physiological Roles and Potential Regulatory Mechanisms*—As first established in kidney, various organs also express multiple Aquaporins. The eye expresses at least three (AQP1, AQP4, and AQP5) in addition to the functionally undefined homolog, MIP. The localization of each is highly specific, with different homologs being expressed in adjacent tissues (e.g., corneal epithelium and endothelium, lens epithelium, and fiber cells). No tissue has been found with overlapping expression of two or more different Aquaporins at the same cellular location, implying that each plays a particular role in vision. AQP5 appears to be involved in lacrimation and corneal desiccation, consistent with the presence of water channels demonstrated in these locations. Previous studies documented expression of AQP1 (CHIP) in the endothelium of capillaries in the soft tissues surrounding salivary glands, but absence of the protein from the gland (Nielsen et al., 1993b, Li et al, 1994). This suggests that water drawn from surrounding capillaries is secreted by the glandular epithelium and is not reabsorbed in excretory ducts. Northern blots of trachea and distal lung both contained strong AQP5 signals (FIG. 16). The specific distribution was not resolved by in situ hybridization and will require immunohistochemical analysis.

The driving force for water movement is presumably provided by the osmotic gradients which result from evaporation of water from the cornea or transport of ions by glandular epithelia (reviewed by Nauntofte (1992)). Nevertheless, there appears to be adrenergic regulation of AQP5, since salivation and lacrimation are known to be controlled by the autonomic nervous system (reviewed by Baum, 1987, *J. Dent. Res.,* 66, 628–632). Sequence comparisons of the mammalian Aquaporins revealed that AQP5 is least closely related to AQP1 and AQP3 whose products are thought to be constitutively active water channels; in contrast, AQP5 is most closely related to AQP2 (Table 3). The cellular distribution of AQP2 is known to be regulated by antidiuretic hormone which increases cellular cAMP levels (Nielsen et al., 1993c, *Proc. Natl. Acad. Sci. U.S.A.,* 90:11663–11667), and the COOH terminus of AQP2 contains a cAMP-protein kinase consensus similar to that within loop D of AQP5. It is not clear whether the cAMP-protein kinase consensus on AQP2 is required for this response or whether direct phosphorylation of the channel can modulate its activity, but AQP5 appears to be regulated by an adrenergic hormone-cAMP cascade analogous to that of antidiuretic hormone and AQP2. The deduced amino sequence for AQP5 will permit development of specific reagents needed to confirm this.

Knowledge of the DNA and amino acid sequence of a protein essential for water transport enables the design of drugs specifically targeted for use in therapy. Such drugs include agonist and antagonists of Aquaporin-1 or Aquaporin-5.

By using the oocyte-swelling assay, the $^3H_2O$ assay, the proteoliposome assay or the red cell membrane assay, or a combination of these assays to measure water permeability, potential pharmacological agents may be screened for specific effects on AQP5 function. Monoclonal antibodies specific for epitopes present on the exofacial loops of AQP5 may be screened for their ability to inhibit water channel activity upon binding. Since organomercurials are known to inhibit water channel activity, reagents with structures related to organomercurials, such as p-chloromercuribenzene sulfonate, are promising inhibitors. The primary sequence of AQP5 provided herein permits the design of specific agonists or antagonists.

Antagonists of the AQP1 water channel are useful for diuresis of patients with congestive heart failure or kidney failure or fluid retention. Patients with sickle cell anemia are known to have subpopulations of erythrocytes which are dehydrated and vulnerable to enhanced sickling. Inhibition of red cell shrinking or enhancement of red cell swelling will prevent this. Organomercurials are known to inhibit water channel activity. In this regard, it has been found that expression of in vitro transcribed AQP1 confers $HgCl_2$-sensitive water permeability to Xenopus oocytes.

Agonists of AQP5 function are also clinically useful. Patients with cystic fibrosis are known to suffer from deficient fluid secretion in the lung and gut. Cystic fibrosis is generally recognized to be due to a mutation in a membrane protein; agents which enhance water secretion would ameliorate some clinical difficulties of this disorder.

Agonists or antagonist of the AQP1 or AQP5 water channels are administered therapeutically in single or divided doses in an amount effective to increase or decrease water absorption, as the case may be for the disease state being treated. The dose, in mg/kg of body weight, as well as length of treatment are readily determinable by the skilled practitioner and is related to the amount of the drug required to inhibit water transport in the model system.

In therapeutic use, administration may be by any route whereby drugs are conventionally administered. Such routes of administration include intraperitoneally, intravenously, intramuscularly, subcutaneously, topically, orally and by inhalation of aerosolized AQP1 or AQP5 agonists or antagonists.

Typical preparation for administration include sterile aqueous or nonaqueous solutions, suspension and emulsions. Examples of nonaqueous solvents are propylene glycol, polyethylene glycol, vegetable oils such as olive oil and injectable organic esters such as ethyl oleate. Aqueous carriers include water alcoholic/aqueous and buffered media. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Oral preparations, such as in capsules, tablets, and other forms, include additives such as cellulose, silica gel and stearic acid.

Inhalation of aerosolized AQP5 agonists recommends itself for the treatment of cystic fibrosis. Local acting agonists may be used in the stimulation of salivary gland secretion in patients with Sjogrens syndrome or following irradiation by patients with head and neck tumors. Topical AQP1 or AQP5 antagonists can be applied to the eye to reduce anterior chamber secretion in patients with glaucoma.

A DNA sequence corresponding to AQP5 may be inserted into an expression vector suitable for gene therapy, such as adenovirus, using well known recombinant DNA techniques, including those described above, and introduced into cells deficient in water secretory channels of the type encoded by AQP5. Gene therapy may be effective in one or more of the following situations. Following radiation therapy of head and neck cancer, patients often suffer inanition and aspiration due to the inability to produce saliva. Dysfunction of salivary glands may be due to insufficient amounts of AQP5 in the glands, and genetic reconstitution of AQP5 by introduction of expression constructs packaged in adenovirus vectors would then permit restoration of this function. Dry eyes is a common affliction affecting adults, particularly women. Dysfunction of lacrimal glands may be due to insufficient amounts of AQP5 in the glands, and genetic reconstitution of AQP5 by introduction of expression constructs packaged in adenovirus vectors would then permit restoration of this function. Premature infants often suffer respiratory insufficiency due to the inability of the airways to conduct water in the immature state. Dysfunction of pulmonary structures may be due to insufficient amounts of AQP5 in the glands, and genetic reconstitution of AQP5 by introduction of expression constructs packaged in adenovirus vectors would then permit restoration of this function.

Topical AQP1 antagonists can be applied to the eye to reduce anterior chamber secretion in patients with glaucoma. Unabsorbable antagonists of AQP1 are useful in the treatment of diarrheal diseases. Parenteral antagonists are useful as diuretics in preventing renal tubular water absorption in patients with renal failure and in the treatment of circulatory overload in congestive heart failure. Parenteral antagonists are also useful in reducing endothelial water uptake and vascular resistance. Inhibitors which act upon AQP1 in arterial endothelium can be used to reduce blood pressure. In addition, inhibitors acting on Aquaporin in the choroid plexus reduce secretion of cerebrospinal fluid and therefore may be used for the treatment of hydrocephalus or following head injury. Alteration of sweat gland function using AQP1 is useful for acclimatization and prevention of heat shock.

Since it is likely that the vasopressin-sensitive water channel is related to the primary sequence of AQP1, the use of AQP1 cDNA for hybridization under low stringency conditions as well as for the design of primers for polymerase chain reaction amplification of reverse-transcribed RNA from the distal nephron can be used to isolate other human homologs.

While it is not yet known which clinical syndromes may be related to abnormalities of AQP1, it is considered likely that mutations of the AQP1 will be manifested by hemolytic anemia, renal dysfunction, or both. Localization of the chromosomal AQP1 locus is underway. Once candidate diseases are identified, the AQP1 cDNA sequence will be useful for restriction fragment length polymorphism analysis in genetic linkage studies. These studies may provide a novel diagnostic method for identification of patients or carriers.

There is very strong homology between AQP1 with proteins isolated and cloned from diverse plant species including pea plants, tobacco roots and several other species. Certain plant homologs such as TUR (Guerrero et al., 1990, *Plant Mol. Biol.* 15:11–26) are known to be induced by drought conditions. The swelling assays reported may be adapted to assess the ability of plant homologs to function as water channels. Those plant proteins shown to function as water carriers can be mutagenized in vitro to optimize water uptake. Recombinant plants can be developed with increased expression of AQP1 homologs which would be expected to have enhanced ability to absorb water and thereby withstand drought.

EXAMPLES

Example 1

Preparation and purification of CHIP28. Human erythrocytes were obtained from blood-bank units stored up to 5 weeks at 4° C. All membrane preparations employed the methods described by Bennett (*Methods Enzymol.* (1983) 96:313–324) which included hypotonic lysis, spectrin-action elution and preparation of stripped membrane vesicles with 1M KI.

KI-stripped erythrocyte membrane vesicles from 1 unit of erythrocytes were suspended to 400 ml in 1% (w/v) sodium N-lauroylsarcosine, 5 mM NaPO$_4$, pH 7.4, 1 mM dithiothreitol, 1 mM NaN$_3$, 1 mM NaEDTA (final concentrations) and incubated for 60 minutes at 22° C. The solubilized proteins were separated from the insoluble pellet by centrifugation for >6 hours at 30,000×g. The pellet was washed by suspending to 1.5 liters in 10 mM NaPO$_4$, pH 7.4, and another centrifugation. The pellet was partially solubilized by shaking for 7 hours at 22° C. in 400 ml of 3% (v/v) Triton X-100, 20 mM Tris-HCl, 1 mM NaN$_3$, 1 mM dithiothreitol, pH 7.8. A significant pellet remained after centrifugation at 30,000×g for >6 hours. The supernatant was removed and filtered through a 0.2 µm filter and loaded onto a 1.6×35 cm column packed with Q-Sepharose which had been equilibrated with the same buffer at 4° C. The column was eluted at 50 ml/hour with a 250 ml linear gradient of 0–0.4M NaCl in the same buffer; pure 28kDa eluted near the end of the gradient. Smaller scale purifications were performed similarly using one-tenth volumes at each step and employing a Mono Q column.

CHIP28 was purified in larger amounts in denatured form by solubilizing the N-lauroylsarcosine insoluble pellet (above) in 200 ml of 1% (w/v) sodium dodecyl sulfate (SDS), 10 mM NaPO$_4$, pH 7.4, 1 mM NaN$_3$, 1 mM dithiothreitol for 60 minutes at 22° C. The soluble proteins were removed after centrifugation at 30,000×g for >6 hours, filtered, and loaded onto a 1.6×30 cm column packed with hydroxyapatite. The column was eluted at 25 ml/hour at 22° C. with a 300 ml linear gradient of 0.3–0.8M NaPO$_4$ in the same buffer; the peak containing both 28kDa and gly28kDa eluted midway through the gradient. The peak fractions were concentrated, dialyzed against 0.2% (w/v) SDS, 10 mM NaPO$_4$, pH 7.4, 1 mM NaN$_3$ and electrophoresed into two 0.3×14×16 cm preparative 12% SDS-polyacrylamide gel electrophoresis (PAGE) slabs. The slabs were cut into 6mm horizontal strips which were eluted with 5ml of the same buffer by shaking overnight at 22° C.

The products of purification were 99% pure, as assessed by silver staining of SDS-PAGE slabs.

CHIP28 does not correspond to any of the previously described erythrocyte membrane proteins seen on Coomassie Blue-stained SDS-PAGE slabs (Steck (1974) *J. Cell Biol.* 62:1–19). When identical SDS-PAGE slabs were stained with Coomassie or silver reagent, a striking number of polypeptides became visible on the silver-stained slabs including a prominent band or narrowly spaced doublet at M$_r$ 28,000.

Although CHIP28 is surprisingly abundant (approximately 200,000 copies/erythrocyte), it has apparently escaped previous discovery due to its poor Coomassie staining.

Example 2

Determination of NH$_2$-terminal amino acid sequence of CHIP28. NH$_2$-terminal amino acid sequence was determined from 28kDa and gly28kDa proteins purified by the procedures described above, and quantitative protein determinations were performed by the method of Lowry et al., 1951, *J. Biol. Chem.* 193:265–275) using bovine serum albumin as a standard. Pure CHIP28 protein (20–60 µg of protein) was precipitated in chilled ethyl alcohol. NH$_2$-terminal amino acid sequence analysis was carried out using an Applied Biosystems model 470A protein sequenator.

NH$_2$-terminal amino acid sequence determination was carried out on six different samples of purified CHIP28 protein, and a consistent sequence was obtained from all preparations.

When the NH$_2$ termini of CHIP28 protein and MIP were aligned, 13 of the 35 amino acids were found to be identical. Comparison of the NH$_2$-terminal amino acid sequences of CHIP28 (AQP1) and MIP are shown below.

CHIP28: ASEFKKKLFWRAVVAEFLATTLFVFISI GXALGFK

MIP: MWELRSASFWRAICAEFFASLFYVFFGLGAS LRWA

Identification of amino acid sequence homologies between MIP and the products of other genes from diverse species suggest that they belong to a family of transmembrane proteins which form channels permeable to small molecules. Two transmembrane channel-forming proteins of approximate molecular mass 28kDa have been identified which share sequence homologies with MIP. The glycerol facilitator from *E. coli* (GlpF) forms a channel in the inner membrane which is permeable to small uncharged molecules, including glycerol (Mura imatsu et al., 1989, *Nucleic Acid Res.* 17:4378). A transmembrane protein (nod 26) is formed in the nitrogen fixing root nodules of soybeans after the symbiotic infection with *Bradyrhizoblum japanicum,* and nod 26 is thought to form multisubunit channels permeable to nutrients (Fortin et al., 1987, *Nucleic Acid Res.* 15:813). New members of the MIP channel family have recently been identified in Drosophila and bacteria, and several have been identified in plants (Baker et al., 1990, *Cell* 60:185–186). MIP may be considered the prototype of an ancient but recently recognized family of membrane channels. These proteins are believed to form channels permeable to water and possibly other small molecules. Analysis of the cDNA sequences from these proteins suggests that they arose from the gene of an ancestral prokaryotic channel protein (Baker, 1990, *Cell* 60:185–186). Although less notable than the homology with MIP, GlpF and nod 26 have amino acid sequence homologies with CHIP28.

Example 3

Isolation of cDNA encoding CHIP28. The probe used to isolate the CHIP28 cDNA was prepared by a three-step PCR amplification of human fetal liver DNA template. Degenerate primers were designed corresponding to proximal and distal segments of the N-terminal amino acid sequence of purified CHIP28 protein. Nondegenerate primers were used with λ phage primers in steps 2 and 3 to amplify the 5' and 3' sequences. The fetal liver PCR products were subcloned into Bluescript vectors (pPCR-1, pPCR-2, and pPCR-3). pPCR-3 was used as a probe to isolate a single positive plaque from 250,000 phage in a λgt10 adult human bone marrow cDNA library. The 2.9 kb bone marrow insert was subcloned (pCHIP). The sequences of pPCR-2 and pCHIP partially overlap and together contain the sequence of the entire 269 amino acid CHIP28 protein. The sequence of pPCR-2 contains a strong homology with the consensus for translational initiation (Kozak, 1987, *Nucleic Acid Res.* 15:8125–8132), followed by the nucleotide sequence in coding the first 22 amino acids of the purified CHIP28 protein that lacks the N-terminal methionine. A more detailed description follows.

Oligonucleotide primers for polymerase chain reaction (PCR) cloning. Oligonucleotide primers were synthesized on an Applied Biosystems 380B DNA synthesizer. Primers A–B contained 5' extensions with restriction sites (underlined below) to facilitate cloning the PCR products. Degenerate sense primer A (5'-CT TCTAGA-TTCTGGAGGGCCGTSGTSGCNGA-3') corresponds to amino acids 9–16 (Phe-Trp-Arg-Ala-Val-Val-Ala-Glu), and degenerate antisense primer B (5'-TA ATCGAT-CCCRATRSWRATRAASACRAA-3') corresponds to amino acids 22–29 (Phe-Val-Phe-Ile-Ser-fle-Gly) determined by microsequencing purified CHIP28 protein. Degeneracy is denoted as follows: R=A and G; S=G and C; N=T, C, A, and G; and W =A and T. Antisense primer C (5'-GCTCTAGA-AGAGGGTCGTGGCCAGGAACTC-3') and sense primers D (5'-GC TCTA-GAGTTCAAGAAGAAGCT CTTCTGG-3') and E (5'-CGGGATC-CTCTTCTGGAGGGCAGTGGTGGCC-3') correspond to the nucleotide sequences identified in the first and second PCR cloning steps. Primers λ-L (5'-GGTGGCGACGACTCCTGGAGCCCC-3') and λ-R (5'-TTGACACCAGACCAACTGGTAATG-3') correspond to sequence on the left and right arms flanking the EcoRI cloning site of λgt11.

Plasmid constructions, fetal liver PCR clones. The cloning of CHIP28 from fetal liver was performed by a three-step PCR strategy. The template for each step was 2–10 ng of DNA from a λgt11 human fetal liver cDNA library (provided by Bernard Forget, Yale University). Control reactions contained nonrecombinant phage λ DNA. In step 1, PCR amplification was made with degenerate primers A and B to determine the 19-bp sequence between their sites on the cDNA (1 minute at 94° C., 1 minute at 50° C., and 1 minute at 72° C.; 25 cycles). The PCR products of the expected size (70–90 base pairs (bp)) were eluted from an acrylamide gel, cloned into pBluescript II (Stratagene), and transformed into bacteria. Plasmid DNA was sequenced from five colonies, and one (pPCR-1) contained a 19-bp insert corresponding to the intervening amino acid sequence (Phe-Leu-Ala-Thr-Thr-Leu) from which antisense primer C was designated.

In step 2, PCR amplifications were designed to determine the nucleotide sequence of the 5' end of the CHIP28 cDNA. First antisense primer B and primer λ-L were used to enrich the template mixture (1 minute at 94° C., 1 minute at 54° C., and 1 minute at 72° C.; 30 cycles). An aliquot was then amplified with antisense primer C and primer λ-L (30 cycles). The PCR products were cloned into pBluescript II and transformed into bacteria, and colony lifts on Colony/Plaque Screen membranes (DuPont) were probed with $^{32}$P-end-labeled primer A. DNA sequencing was performed on plasmid DNA isolated from seven colonies that hybridized strongly with primer A, and one insert of 110 bp corresponded to the 5' end of CHIP28 cDNA (pPCR-2). Partially overlapping sense primers D and E were derived from this sequence.

In step 3, PCR amplifications were designed to determine the nucleotide sequence of the 3' end of the CHIP28 cDNA. First, sense primer D and primer λ-R were used to enrich the template mixture (1 minute at 94° C., 1 minute at 65° C., and 3.5 minutes at 72° C.; 35 cycles). DNA molecules >500 bp were purified by using the GeneClean II kit (Bio 101, La Jolla, Calif.) and amplified with sense primer E and primer λ-R (30 cycles). An aliquot of the final reaction was analyzed by Southern analysis with $^{32}$P-end-labeled primer C as probe. A single 850-bp product that hybridized with primer C was cloned into pBluescript II. The plasmid DNA was completely sequenced on both strands (pPCR-3). This clone contained sequences corresponding to the known N terminus and the distal amino acid sequence of CHIP28 protein.

Isolation of a CHIP28 cDNA from human bone marrow. The insert from pPCR-3 was gel-purified, labeled with [α-$^{32}$P]dCTP (6,000 Ci/mmol, Amersham; 1 Ci=37 GBq) by using a random priming kit (Pharmacia LKB), and used to probe 2.5×10$^5$ plaques of an adult human bone marrow cDNA library in λgt10 (Clontech) on Colony/Plaque Screen membranes. A single positive plaque was isolated, and the 2.9-kb insert was subcloned into pBluescript II (pCHIP).

Preparation of pCHIP deletion and expression constructs. Approximately 1.6 kb was removed from the 3' end of pCHIP with HindIII. The resulting 1.3-kb EcoRI-HindIII fragment containing the 5' end of CHIP28 cDNA was used to make a series of exonuclease III deletion constructs for DNA sequencing. (Herikoff (1984) *Gene* 28:351–359). The exonuclease III construct containing nucleotides 594–826 (encoding the last 70 amino acids of the pCHIP reading frame, the stop codon, and 14 bp of 3' untranslated sequence) was used to prepare the β-galactosidase/CHIP28 expression constructs. The 232-bp SmaI-SmaI fragment was cloned into the SmaI site of pBS (Stratagene), and plasmids with a single SmaI insert were sequenced. CHIP28-3' inserts were obtained in frame with β-galactosidase or in the reverse orientation. The in frame construct was expressed in bacteria and a 12kDa protein was shown by immunoblot to react with affinity-purified antibody specific for the C terminus of CHIP28. This confirms that the nucleotide sequence encoded the authentic amino acid sequence of the C terminus of the CHIP28 protein.

DNA sequencing and analysis. Double-stranded DNA sequencing was performed by using Sequenase 2.0 (United States Biochemical) and [α-$^{35}$S]dATP (1,000 Ci/mmol; Amersham).

FIG. 1 is a diagram representing the second-step fetal liver PCR product (pPCR-2), the 2.9-kb insert isolated from the human bone marrow library (pCHIP), and the restriction and exonuclease fragments from which nucleotide sequences were obtained (arrows).

FIG. 2 shows the 5' untranslated nucleotide sequence, the open reading frame, the first 500 bp of the 3' untranslated sequence, and the 269 amino acid sequence of CHIP28 deduced from pPCR-2 and pCHIP, and the terminal 3' untranslated nucleotide sequence with the major polyadenylation signal AATAAA. The stop codon is represented by ". . . ". Amino acid residues determined by microsequencing of the purified CHIP28 protein are underlined in FIG. 2.

Figure 3:
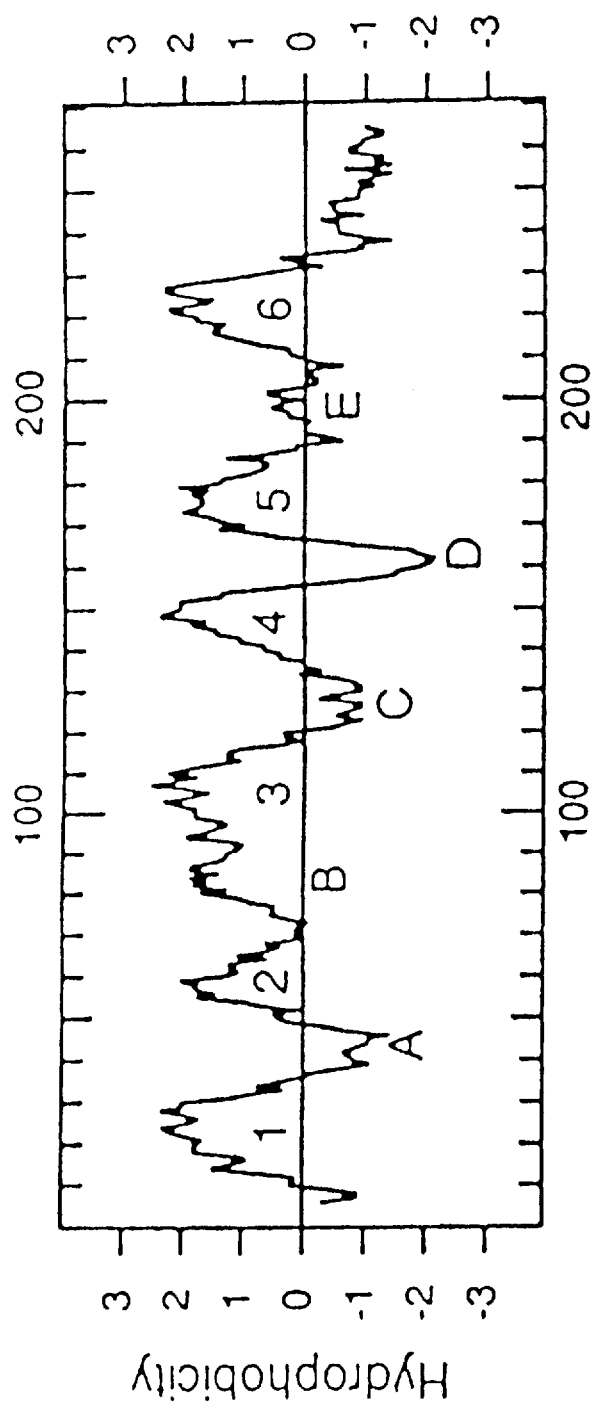
FIG. 3 shows a computer analysis of the deduced amino acid sequences which demonstrates six strongly hydrophobic regions.

FIG. 3 shows a computer analysis of the deduced amino acid sequence using the algorithm of Kyte et al. (1982) *J. Mol. Biol.* 157:105 132) which demonstrated six strongly hydrophobic regions that most likely correspond to bilayer spanning domains.

Figure 4:
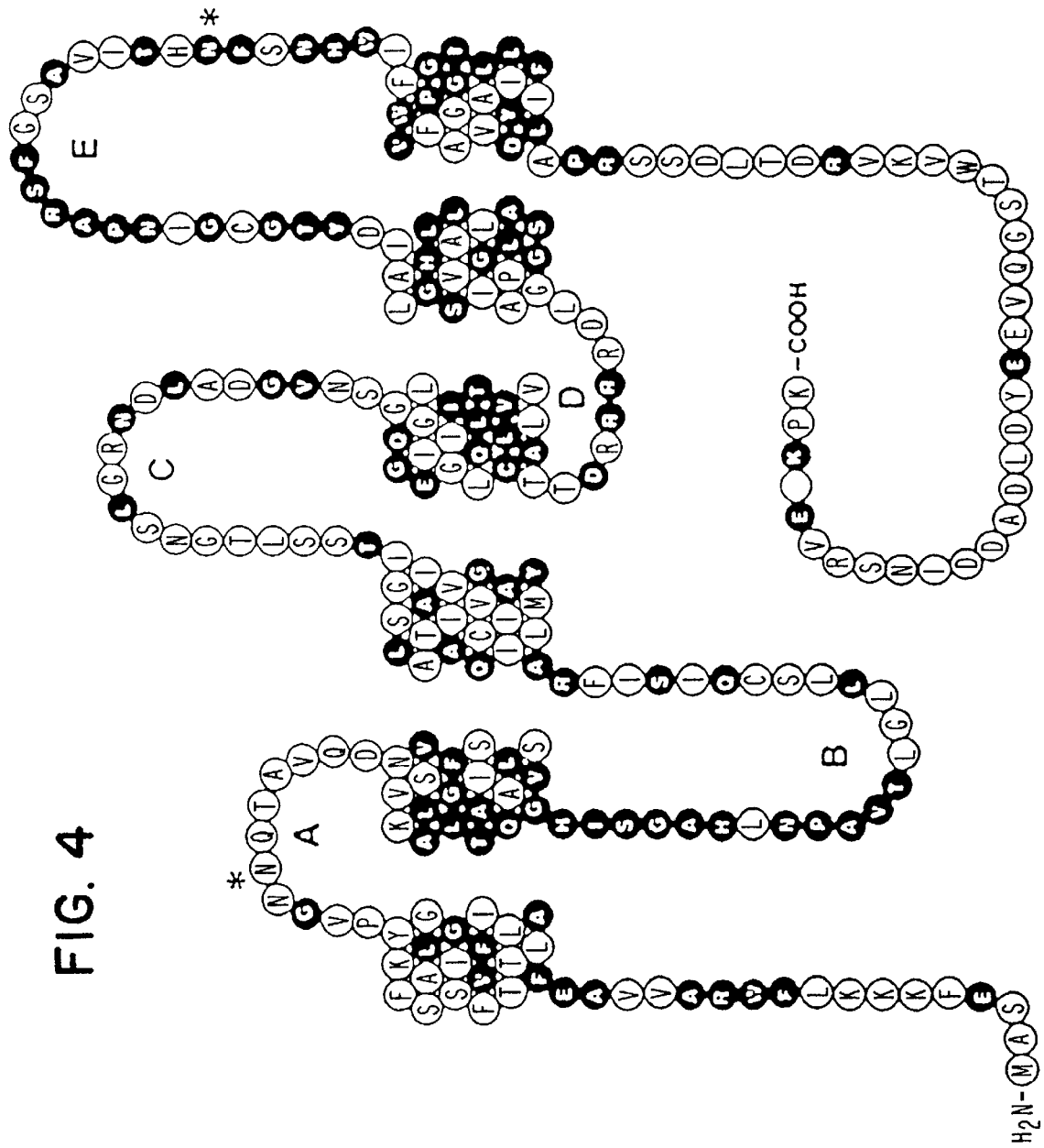
FIG. 4 shows the proposed membrane topology of AQP1 SEQ ID NO:17.
Figure 5:
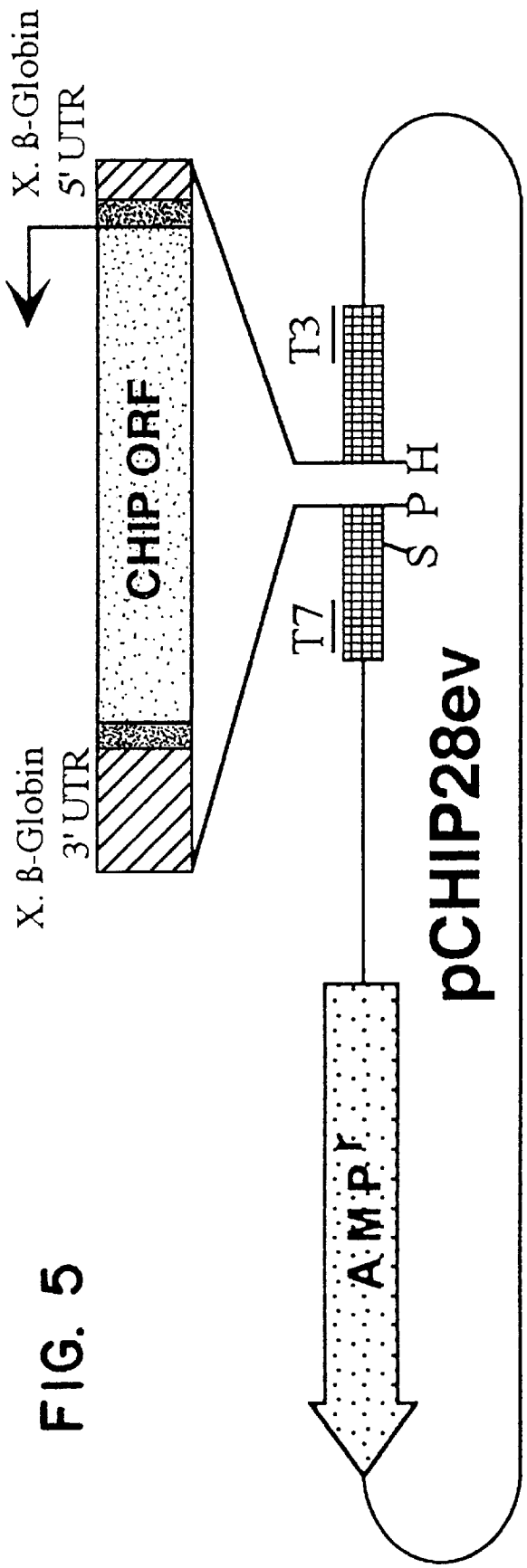
FIG. 5 shows a diagram of AQP1 expression construct.

A proposed model of membrane topology of CHIP28 is shown in FIG. 4. In FIG. 4, loops A, C and E are exofacial; loops B and D and the amino and carboxy termini are endofacial. The two potential glycosylation sites are marked by an asterisk. Residues denoted by a black background with white letters indicate residues which are identical in CHIP28 and MIP.

The amino acid sequence of CHIP28 was used to search for homologies in the GenBank DNA database with the TFASTA program. Computer search of the GenBank DNA database identified a strong homology with MIP. When the N termini are aligned, the deduced amino acid sequences of the two proteins are 42% identical overall (see FIG. 4). However, while the C-terminal cytoplasmic domains of the two proteins are of nearly identical size, only 4 of the 35 C-terminal residues are shared.

The CHIP28 integral membrane protein of the invention exists in approximately 200,000 copies per red cell and is also very abundant in proximal convoluted renal tubules where it comprises 3.8% of the total protein in brush border membrane vesicles. The physical behavior of CHIP28 under nondenaturing conditions indicates that it is similar to membrane channels, existing as a tetramer with one subunit bearing an asparagine-linked polylactosaminoglycan. The cDNA for 28kDa which has now been isolated encodes a 269 amino acid integral membrane protein which is distantly related to bovine lens MIP and a group of membrane proteins recently identified in plants. Expression of TUR, a MIP homolog expressed in the roots of pea shoots, was found to be induced by water deprivation (Guerrero et al. (1990) *Plant Mol. Biol.* 15:11–26). The structure of CHIP28 includes an internal repeat with the first three bilayer-spanning domains being oriented at 180° to the second. This curious inversion indicates that the protein has a bidirectionally active function.

In order to facilitate a more complete understanding of the invention, a number of Examples are provided below. However, the scope of the invention is not limited to specific embodiments disclosed in these Examples, which are for purposes of illustration only.

Example 4

This example shows that expression of red blood cell AQP1 protein confers water channel activity to Xenopus oocytes.

Preparation of expression construct. An expression construct was prepared by ligating the coding sequence of the AQP1 cDNA between the 5' and 3' untranslated flanking sequences of the Xenopus β-globin cDNA. DNA that contained the entire coding sequence of AQP1 protein was formed by three-way ligation of (i) a 60-bp EcoRl-XmnI DNA fragment containing nucleotides −38 to +22 (pPCR-2 disclosed in U.S. application Ser. No. 07/930,168, incorporated herein by reference) and (ii) an 800-bp XmnI-SmaI DNA fragment containing nucleotides +23 to +822 (pCHIP) of AQP1 cDNA (Preston and Agre, 1991, *Proc. Natl. Acad. Sci. U.S.A.* 88:11110) with (iii) EcoRI-SmaI-digested pBLUESCRIPT II (Stratagene). The blund-end 860-bp EcoRI-SmaI DNA fragment was ligated into the BglII site of pSP64T (Krieg and Melton, 1984, *Nucleic Acids Res.* 12:7057). A 1.1-kb HindIII-PstI DNA that contained the AQP-1 cDNA coding sequence in frame with the 5' and 3' untranslated sequences of the Xenopus adult β-globin gene was ligated into pBLUESCRIPT II. Conventional molecular genetic techniques were used (J. Sambrook et al., 1989, *Molecular Cloning: A Laboratory Manual,* Cold Spring Harbor Laboratory, Cold Spring Harbor, N.Y.) with commercially available restriction endonucleases and DNA ligase (Gibco BRL). Confirmation of the recombinants was made by enzymatic nucleotide sequencing (U.S. Biochemical). Capped RNA transcripts were synthesized in vitro, and the RNA was purified as described by Yisraeli and Melton, (*Methods Enzymol.,* 1989, 180:42). Sense AQP1 RNA was synthesized with T3 RNA polymerase and SmaI-digested CHIP28 expression vector, and antisense AQP1 RNA was made with T7 polyrnerase from Hind III-digested vector.

Expression of AOP1 in Xenopus oocytes. Oocytes were removed from female *Xenopus laevis* frogs and prepared as described by Dascal (CRC *Crit. Rev. Biochem.,* 1987, 22:317–373). Oocytes were injected with 0.05 microliters of water (control) or the same volume of water containing 1–10 nanograms of AQP1 RNA. The oocytes were incubated for up to 96 hours at 18° C. in modified Barth's buffer (88 mM NaCl, 1 mM KCl, 0.8 mM $MgSO_4$, 0.3 mM $Ca(NO_3)_2$, 0.4 mM $CaCl_2$, 2.4 mM $NaHCO_3$, 10 mM HEPES, pH =7.4, total osmolality =200 mOsm/kg) also containing antibiotics. The whole oocytes were then removed and total cellular protein was dissolved in 40 microliters of buffer containing 1% (w/v) SDS and analyzed by immunoblot (Towbin et al., 1979, *Proc. Natl. Acad. Sci. USA* 76:4350–4354).

Expression of AQP1 was monitored by immunoblot with an antibody to the COOH-terminal cytoplasmic domain of AQP1. Antibodies were prepared as described by Denker et al. (*J. Biol. Chem.,* 1988, 263:15634). A 28-kD protein was detected with anti-AQP1 24 hours after injection of oocytes with AQP1 RNA, and it increased in abundance for up to 72 hours. A 35- to 45-kD glycosylated form of AQP1 was also apparent.

Figure 6:
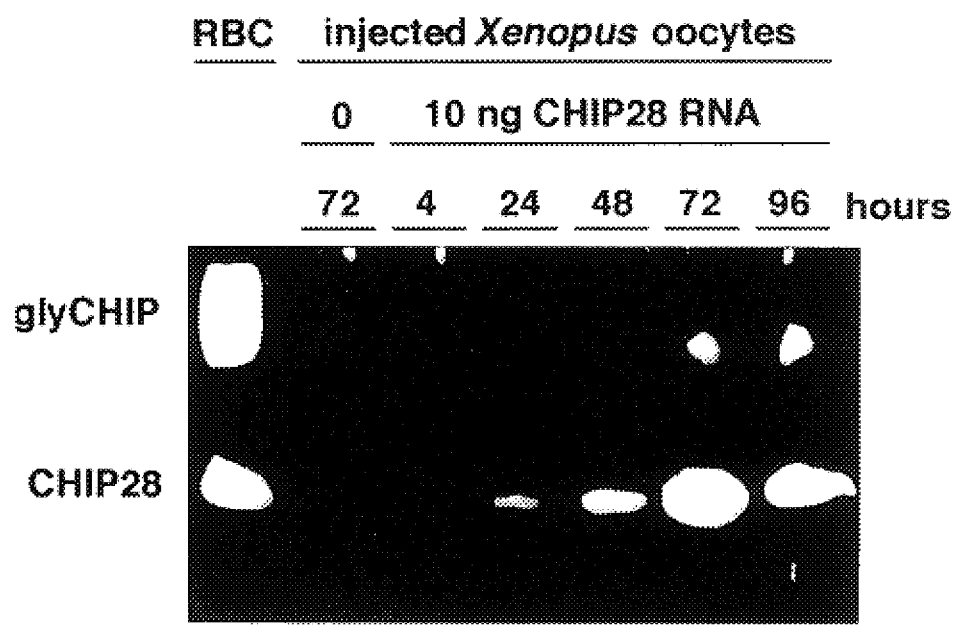
FIG. 6 is an immunoblot showing expression of AQP1 or in oocytes.
Figure 7:
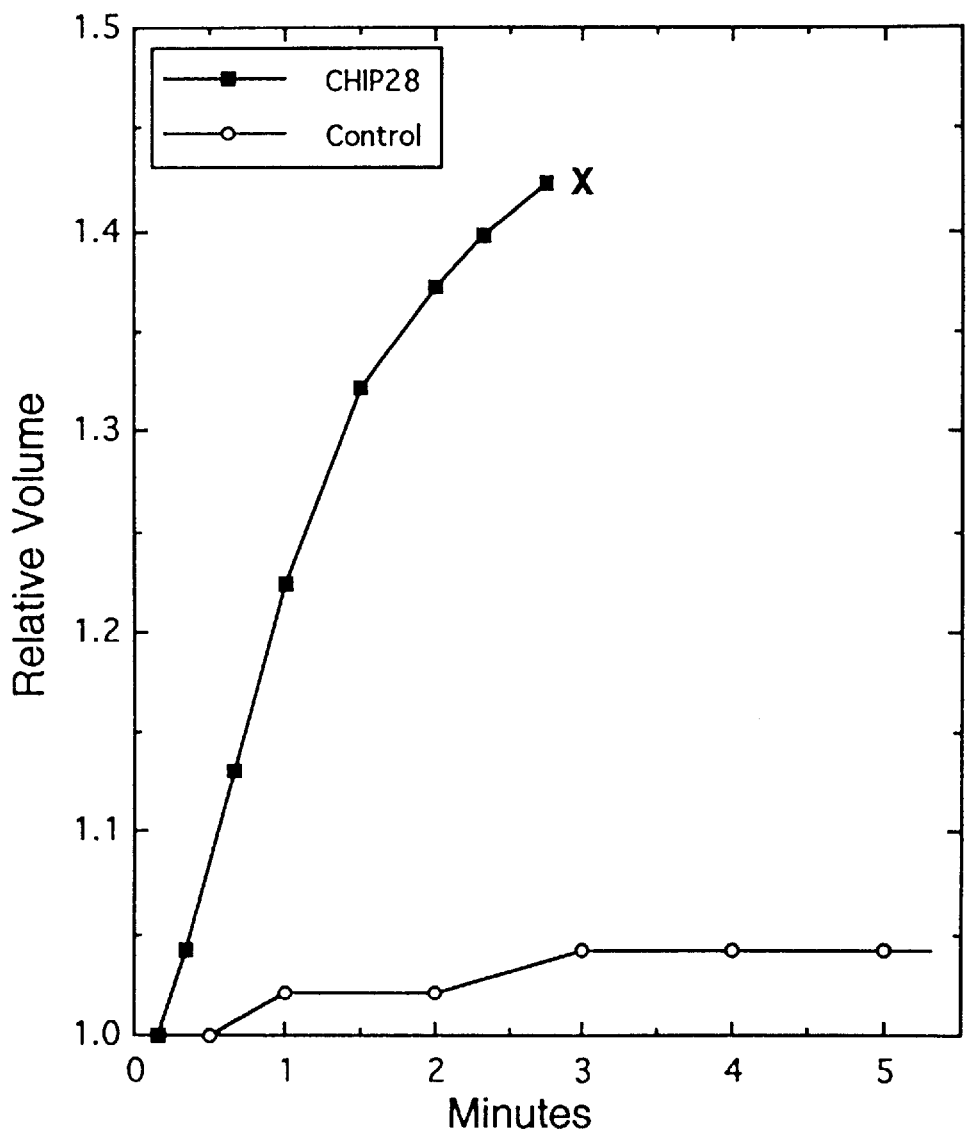
FIG. 7 shows osmotic swelling of control and AQP1 RNA-injected oocytes.
Figure 8:
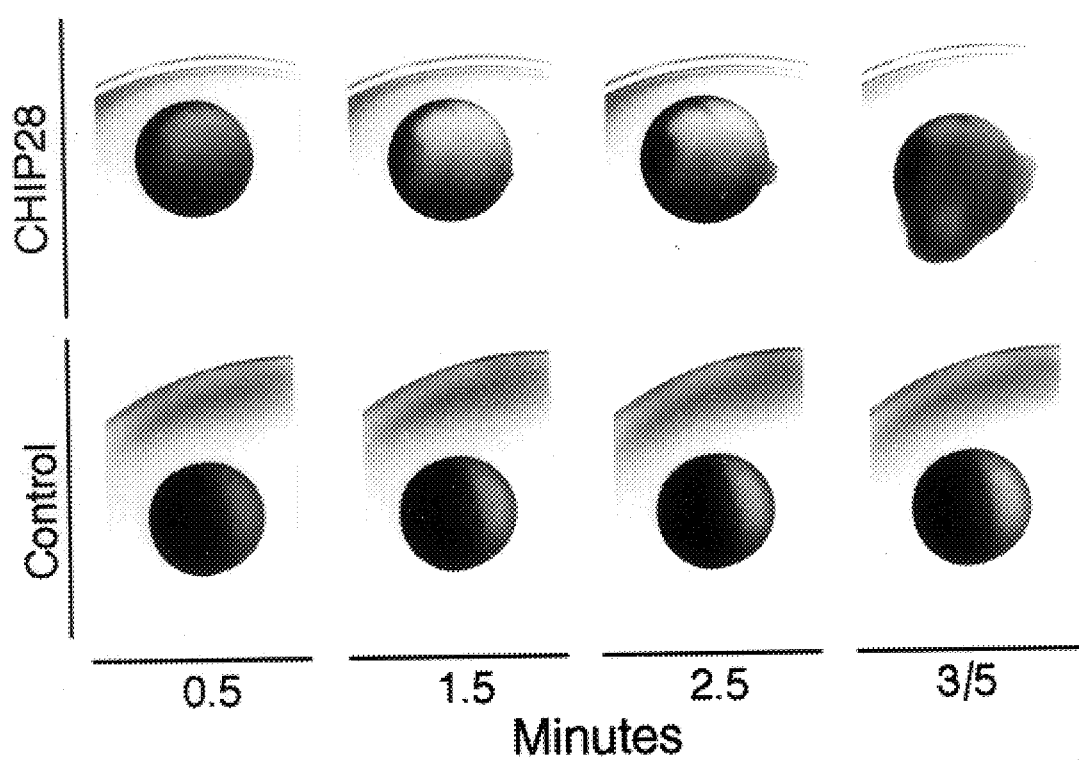
FIG. 8 is a photograph of AQP1 RNA-injected oocytes over time.

FIG. 6 is a contact print of an immunoblot of human RBC membranes and Xenopus oocytes injected with 0 or 10 ng of in vitro-transcribed AQP1 RNA. After incubation for up to 96 hours, the oocytes were homogenized in 1.25% (w/v) SDS (40 $\mu$l), subjected to electrophoresis on a 12% SDS-polyacrylamide gel, and transferred to nitrocellulose. A contact print of an immunoblot of red cell membranes (0.5 $\mu$g of protein) and solubilized oocytes (10 $\mu$l) is shown after incubation with a 1:1000 dilution of anti-APQ1 and visualization with $^{125}$I-labeled protein A (Laemmli, 1970, Nature 227:680; Towbin et al., 1979, *Proc. Natl. Acad. Sci. U.S.A.* 76:4350; Davis and Bennett, 1982, *J. Biol. Chem.* 257:5816). Positions of AQP1 and N-glycosylated AQP1 (gly28kDa) are denoted at the left of the immunoblot. AQP1 protein was identified only in the AQP1 RNA-injected oocytes, which were each found to express approximately $10^{11}$ copies of the AQP1 protein. The electrophoretic mobility of the recombinant AQP1 protein in oocytes was virtually identical to the protein from red cells, including the presence of a glycosylated subpopulation.

Demonstration of water channel activity. Xenopus oocytes are normally relatively impermeable to water, and do not swell despite being laid in fresh pond water. A swelling assay was adapted from that of published work (Fischbarg et al., 1990, *Proc. Natl. Acad. Sci. USA* 87:3244–3247; Zhang et al., 1990, *J. Biol. Chem.* 265:15375–15378). Control-injected oocytes and AQP1 RNA-injected oocytes were incubated at 22° C. in modified Barth's solution diluted with distilled $H_2O$ to 30% of the original tonicity. The oocytes were then observed by videomicroscopy. Swelling was monitored with a Nikon phase-contrast microscope equipped for videorecording. The longest (D1) and shortest (D2) diameters of the oocytes were measured at 15- to 30-second intervals. Oocyte volumes (V) at each time point were calculated relative to volume at the initial observation ($V_0$):

$$V/V_o = (D1 \times D2)^{3/2}(D1 \times D2)^{3/2}/(D1_o \times D2_o)^{3/2}$$

The change in relative volume with time, $d(V/V_o)/dt$, up to 8 minutes (or time of oocyte rupture) was fitted by computer to a quadratic polynomial, and initial rates of swelling were calculated. Osmotic water permeability ($P_f$, in cm/s) was calculated from osmotic swelling data, initial oocyte surface area (S=0.045 $cm^2$), and the molar volume of water ($V_w$=18 $cm^3$/mol) (Zhang et al., 1990, *J. Biol. Chem.* 15375):

$$P_f = [V_o \times d(V/V_0)dt]/[S \times V_w \times (osm_{in} - osm_{out})]$$

The control-injected oocytes swelled minimally and failed to burst even after several hours. The AQP1 RNA-injected oocytes swelled visibly. Within 3–5 minutes, the relative volumes of the AQP1 RNA-injected oocytes reached 150% of the original volume and burst. These findings were reproduced in more than 30 different experiments.

As previously indicated, the membrane water channel is known to be inhibited by submillimolar concentrations of $HgCl_2$ and may be restored by subsequent incubations in 5 mM β-mercaptoethanol (Zhang et al., 1990, *J. Biol Chem.* 265:15375–15378). Swelling of the AQP1 RNA-injected oocytes was found to be inhibited by 0.3 mM $HgCl_2$ and restored by 5 mM β-mercaptoethanol.

Table 1 shows inhibition of osmotic water permeability of AQP1 RNA-injected oocytes with $HgCl_2$, and restoration with β-mercaptoethanol. After 72 hours, control- or AQP1 RNA-injected (10 ng) oocytes were treated as indicated. Some oocytes were left in standard Barth's buffer prior to measurement of osmotic swelling at 22° C. Other oocytes were incubated 5 minutes in Barth's buffer containing 0.3 mM or 3 mM $HgCl_2$ as described, then removed and incubated for 15 min in 5 mM β-mercaptoethanol prior to osmotic swelling in the presence of β-mercaptoethanol.

TABLE 1

| RNA injected | Oocyte treatment $HgCl_2$ (nM) | ME | $P_f$ cm/s x | SD* $10^{-4}$ | N† |
|---|---|---|---|---|---|
| None | 0 | 0 | 27.9 | 18.8 | 8 |
| | 0.3 | 0 | 20.3 | 9.2 | 2 |
| | 0.3 | 5 | 25.4 | 2.2 | 2 |
| AQP1 | 0 | 0 | 210 | 40.7 | 10 |
| | 0.3 | 0 | 80.7 | 3.7 | 3 |
| | 3.0 | 0 | 34.5 | 11.2 | 3 |
| | 0.3 | 5 | 188 | 50.8 | 3 |

*SD, standard deviation.
†N, number of experiments.

Table 2 shows comparisons between the amount of AQP1 RNA injected, osmotic water permeability, and number of copies of AQP1 protein expressed in Xenopus oocytes. After 72 hours, control-injected oocytes and oocytes injected with 0.1 to 10 ng of AQP1 RNA were studied for osmotic swelling at 22° C. The amount of AQP1 protein was estimated by dilutional immunoblotting (Denker et al., 1988, *J. Biol. Chem.* 263:15634; Laemmli, 1970, Nature 227:680; Towbin et al, 1979, *Proc. Natl. Acad. Sci.*, 76:4350; Davis and Bennett, 1982, 257:5816).

TABLE 2

| AQP1 RNA injected (ng) | $P_f$ cm/s x | SD $10^{-4}$ | N | AQP1 expressed* |
|---|---|---|---|---|
| 0 | 13.7 | 3.3 | 3 | 0 |
| 0.1 | 50.0 | 10.1 | 3 | <0.1 |
| 0.5 | 112 | 29.2 | 4 | 0.4 |
| 2.0 | 175 | 38.4 | 4 | 1.6 |
| 10.0 | 221 | 14.8 | 2 | 10 |

*Copies per oocyte x $10^{-11}$

As another demonstration of water channel activity, control arid AQP1 RNA-injected oocytes were incubated in hypotonic (30%) or isotonic Barth's buffer containing 1 $\mu C_i^3 H_2O$. The oocytes were removed at selected time intervals, and the difference between the control and CHP28 RNA-injected oocytes were determined by scintillation counting of the sodium dodecyl sulfate solubilized oocytes. Incubations in hypotonic buffer produce more than a five-fold increase in the uptake of $^3H_2O$ at 22° C. and larger relative increases at lower temperatures. No difference in $^3H_2O$ uptake was noted after incubation of the AQP-1 expressing oocytes if the incubation was performed in isotonic buffer.

These findings demonstrate that the water channel function of Aquaporin family members can be readily observed for water uptake as well as water release, and that the water channel is osmotically driven.

Example 5

By immunoblot analysis and immunohistochemical staining with antibodies specific for CHIP28 and by Northern analysis with the CHIP28 cDNA, the CHIP28 protein and RNA have been demonstrated in kidney where CHIP28 makes up approximately 3.8% of the total brush border of proximal convoluted tubules. The location in proximal but not distal tubules indicates that CHIP28 corresponds to the constitutively active water channel but may not be a component of the vasopressin-sensitive water channel of the distal nephron. Partial sequence of cDNA clones isolated from kidney libraries indicate that the proximal tubule (CHIP28 and red cell CHIP28 have identical nucleotide and deduced amino acid sequences. Northern analysis of RNA from small bowel, lung and heart indicate the presence of CHIP28 in cells within these organs. CHIP28 has been localized in various tissues using CHIP antibodies and immunohistochemicals staining of tissue sections and CHIP28 cRNA probes and in situ hybridizations. To date CHIP28 has been found to be a major membrane protein in the following tissues: vascular endothelium (gut venules, endocardium, and arterial endothelium); pulmonary alveolar and airway epithelium; cilary body and corneal endothelium of the anterior chamber of the eye; sweat glands; and choroid plexus.

Example 6

Purified Aquaporin protein may be reconstituted into liposomes of defined lipid composition to establish directly the role of Aquaporins in water channel function. This example shows that AQP1 protein functions as a molecular water channel and that AQP1 responsible for most transmembrane water movement in RBCs.

Preparation and purification of AQP1. Human erythrocytes were obtained from blood-bank units stored up to 5 weeks at 4° C. Membrane preparation employed the methods described by Bennett (*Methods Enzymol* (1983) 96:313–324) which included hypotonic lysis, spectrin-action elution and preparation of stripped membrane vesicles with 1M KI. KI-extracted membrane vesicles were extracted in 200 ml with 1% (w/v) N-lauroylsarcosine, 1 mM $NH_4HCO_3$, 1 mM $NaN_3$, 1 mM dithiothreitol, and 0.5 mM PMSF by shaking for 1 hour at room temperature and pelleted by centrifugation at 31000×g in a Beckman JA-14 rotor for 4 hours at 4° C. The pellet was washed once in 600 ml of 7.5 mM sodium phosphate, pH 7.4, and centrifuged overnight at 15000×g at 4° C. The pellet was solubilized by shaking for 1 hour at room temperature in 300 ml of chromatography buffer (20 mM Tris-HCl, pH 7.8, 1 mM $NaN_3$, 1 mM dithiothreitol) also containing 3% (v/v) Triton X-100 and was spun at 30000×g for 4 hours. The supernatant was filtered through a 0.22 μm Millex GV membrane (Millipore). The material was separated into five equivalent fractions which were separately loaded onto a 4.6×50 mm POROS Q/H anion-exchange column (PerSeptive Biosystems, Cambridge, Mass.) equilibrated with chromatography buffer containing 0.1% (v/v) Triton X-100 running at 3 ml/minute while attached to a Pharmacia FPLC apparatus. The column was eluted with a 12-ml gradient of 0.2–0.6M NaCl in the same buffer while the optical absorbance was monitored at 280 nm. The major protein peaks eluted at 0.25–0.30M NaCl, and the peaks from five separate runs were combined, diluted with 5 volumes of chromatography buffer containing 1.2% (w/v) octyl glucoside, and readsorbed to the column which was washed until the baseline absorbance was stable (approximately 25 ml). The column was eluted with a 6-ml gradient of 0–0.6M NaCl at the same rate while 0.5-ml fractions were collected. The major peak appeared in two fractions and was comprised of AQP1 (the 28-kDa protein itself and the 35–60-kDa glycosylated protein) when analyzed on SDS-polyacrylamide electrophoresis gels (Laemmli, 1970, Nature 227:680–685) stained with silver.

Small-scale purifications were performed using 24 ml of packed RBCs from whole blood freshly drawn into ACD solution. Centrifugations were performed at 44000×g for 90 minutes in a Beckman JA-20 rotor, but the scaled-down methods were otherwise similar to the large preparations. The N-lauroylsarcosine extracted, washed pellet was directly solubilized in 72 ml of chromatography buffer containing 3% (w/v) octylglucoside by shaking for 1 hour at room temperature. This was pelleted by centrifugation, filtered, and loaded onto the POROS Q/H column equilibrated with chromatography buffer containing 1.2% (w/v octyl glucoside running at 3 ml/minute. The peak from a 12-ml 0.2–0.6M NaCl gradient was diluted into 15 mL in the same buffer (without NaCl) reapplied onto the column, and eluted with a 4-ml gradient of 0–0.6M NaCl while 0.1 ml fractions were collected. The major peak was contained in 0.3 ml and was comprised of AQP1.

Preparation AQP1-containing proteoliposomes. Crude *Escherichia coli* lipid was obtained from Avanti Polar Lipids, Inc., and neutral lipid was removed by acetone/ether wash (Ambudkar & Maloney, 1986, *Methods. Enzymol.* 125:558–563). The purified *E. coli* bulk phospholipid is composed of phosphalidylethanolamine (70%), phosphatidylglycerol (15%), and cardiolipin (15%) (Chen & Wilson, 1984, *Proc. Natl. Acad. Sci. USA* 83:2652–2656). *E. coli* bulk phospholipid was employed since it has previously been used for functional reconstitution of several transport proteins including the glucose transporter of RBCs (Maloney & Ambudkar, 1989, *Arch. Biochem. Biophys.* 269:1–10; Chen et al., 1986, *Proc. Natl. Acad. Sci. USA* 83:2652–2656).

Highly purified AQP1 protein was incorporated into proteoliposomes by detergent dilution; control liposomes were formed in an identical manner without AQP1 protein.

Purified AQP1 was stored overnight at 0° C. or frozen for several days at −80° C. prior to reconstitution. Reconstitution into proteoliposomes was carried out in a final volume of 1 ml containing 60–90 µg of purified AQP 1 protein in chromatography buffer, 9 mg of bath-sonicated *E. coli* phospholipid, 1.25% (w/v) octyl glucoside, and 50 mM Tris-HCl (pH 7.5). The mixture was briefly blended on a vortex mixer and incubated for 20 minutes on ice. Proteoliposomes (or liposomes prepared without protein) were formed at room temperature by rapidly injecting the mixture into 25 ml of buffer A [50 mM MOPS, pH 7.5, 150 mM N-methyl-D-glucamine (NMDG) chloride also containing 10–15 mM carboxyfluorescein, 1 mM dithiothreitol, and 0.5 mM PMSF]. For the measurement of proton permeability, proteoliposomes and liposomes were loaded with buffer B (5 mM MOPS, pH 7.5, 150 mM KCl, 0.5 mM carboxyfluorescein, 1 mM dithiothreitol, and 0.5 mM PMSF). The suspension was incubated for 20 minutes at room temperature. Proteoliposomes or liposomes were collected by centrifugation for 1 hour at 123000×g in a Beckman Type 42.1 rotor at 4° C. The pellet was resuspended in 8 ml of buffer A or B and then centrifuged for 1 hour at 152000×g in a Beckman Type 50 Ti rotor. Proteoliposomes or liposomes were resuspended in 300 µl of buffer A or B and stored at 4° C. for 16–24 hours. Typically 50% (54±6%, n=5) of the AQP1 protein and 70% of the phospholipid were recovered in proteoliposomes. The lipid to protein ratio was in the range of 120:1 to 219:1. These proteoliposomes have internal volumes of 1 µl/mg of phospholipid (Ambudkar and Maloney, 1986, *J. Biol. Chem.* 261:10079–10086). Protein and phospholipid were measured as described by Ambudkar & Maloney (*J. Biol. Chem.*, 1986, 261:10079–10086).

Permeability measurements. Membrane permeability measurements ($P_f$) were measured by exposing AQP1 proteoliposomes or control liposomes to an osmotic gradient by rapid mixing with an equal volume of another solution containing buffer A plus sufficient sucrose to increase osmolality in the mixed solutions to a value 120% of that in the original solution. This was performed with a stopped-flow fluorometer (SF.17MV, Applied Photophysics, Leatherhead, U.K.) with a measured dead time of 0.7 ms. The excitation wavelength was set at 490±1.5 nm using a 150-W mercury-xenon arc lamp and monochromator ($f3.4$ grating monochromator, both from Applied Photophysics); the emission wavelength was >515 nm using a cut-on filter (Oriel Corp., Stratford, Conn.). Extravesicular carboxyfluorescein fluorescence was completely quenched using anti-fluorescein antibody (Harris et al., 1990, *Am. J. Physiol.* 259:F366–F371).

Within the range of osmolalities used in these experiments, the vesicles acted as perfect osmometers, and relative volume (absolute volume divided by initial volume) was linearly related to relative fluorescence (absolute fluorescence divided by initial fluorescence). The data obtained from 8 to 16 determinations was averaged and fit to single-exponential curves using 5 software provided by Applied Photophysics (Zeidel et al., 1992, *Biochemistry* 31:589–596). The fitting parameters were then used to determine $P_f$ by first applying the linear conversion from relative fluorescence to relative volume and then iteratively solving the water permeability equation using MathCAD software (MathSoft, Cambridge, Mass.):

$$dV(t)/dt=(P_f)(\text{SAV})(\text{MVW})[(C_{in}/V(t))-C_{out}] \quad (1)$$

where V(t) is relative intravesicular volume as a function of time, $P_f$ is osmotic water permeability in centimeters per second, SAV is the vesicle surface area to volume ratio, MVW is the molar volume of water (18 cm$^3$/mol), and $C_{in}$ and $C_{out}$ are the initial concentrations of total solute inside and outside the vesicle, respectively (Zeidel et al., 1992, *Biochemistry* 31:589–596).

Measured radii of control liposomes and AQP1 proteoliposomes were determined by electron microscopy and averaged 7.0±0.7×10$^{-6}$ cm. The number of AQP1 molecules per milliliter of suspension was calculated from the amount of protein per milliliter in each preparation and the molecular weight of AQP1 (28,500). The measured total entrapped volume per milligram of phospholipid, the calculated volume of each liposome, and the total number of liposomes per milliliter of suspension were calculated from the total phospholipid content.

Dividing the number of protein molecules per milliliter of suspension by the number of proteoliposomes per milliliter of suspension gave the number of protein molecules per proteoliposome.

The general formula defining solute exit from a vesicle is $$J_{urea}=d(\text{urea})/dt=P_{urea}(\text{SA})\Delta C \quad (2)$$

where $J_{urea}$ is urea flux, $P_{urea}$ is the permeability coefficient for urea, SA is the surface area of the vesicle, and $\Delta C$ is the difference in urea concentration between the inside and outside of the vesicle, which diminishes as the system reaches equilibrium. If $$V_{rel} = V(t)/V_o \quad (3)$$

where $V_o$ is the initial volume of the vesicle and $V(t)$ is the absolute volume at time t, then, under these experimental conditions, it can be shown that $$dV_{rel}/dt = P_{urea}[SA/V_o][0.00134][(1122/V_{rel}) - 1496] \quad (4)$$

Using parameters from the single-exponential curve fit to the data and the relationship between relative volume and relative fluorescence, equation 4 was solved for $P_{urea}$ using MathCAD.

Figure 9:
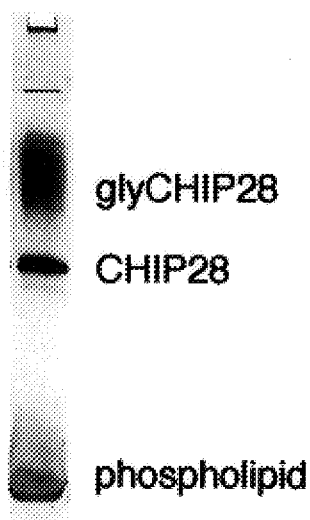
FIG. 9 shows a silver-stained SDS-PAGE slab of proteoliposomes containing purified AQP1.
Figure 10A:
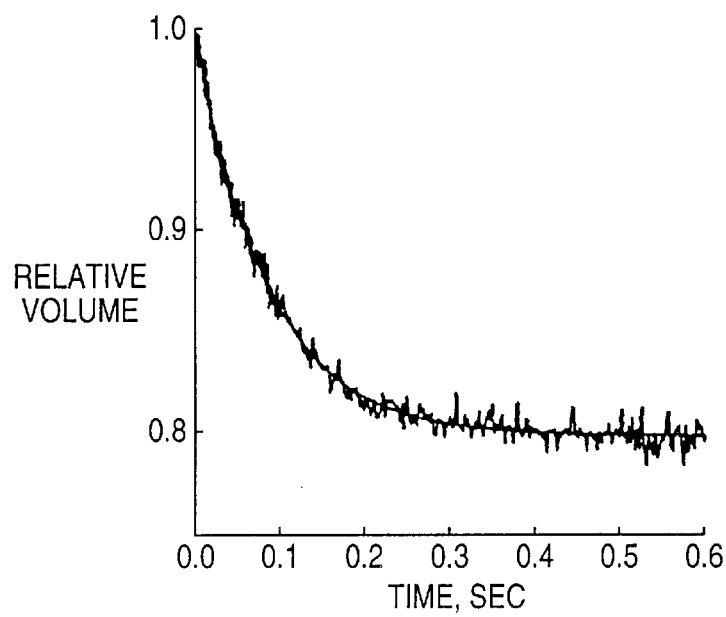
FIGS. 10A, 10B, 10C show water flux in control liposomes and in AQP1-containing proteoliposomes, respectively.
Figure 10B:
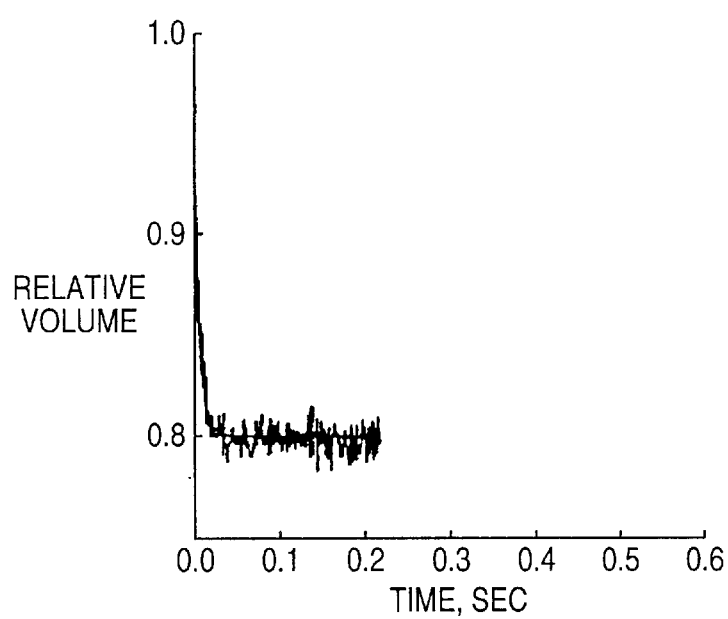
Figure 10C:
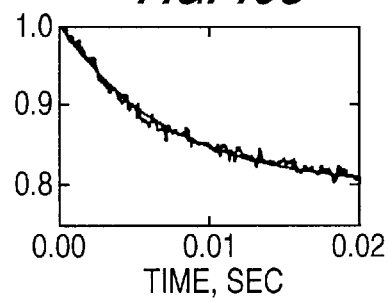

Analysis of AQP1 proteoliposomes in silver-stained SDS-polyacrylamide gel demonstrated that the protein in the proteoliposomes was approximately 98% pure (FIG. 9).

As indicated above, the coefficient of osmotic water permeability, $P_f$, was determined by rapidly increasing the extravesicular osmolality in a stop-flow fluorometer. Water efflux from the vesicles reduced the intravesicular volume, increasing the self-quenching of the carboxyfluorescein. $P_f$ was markedly increased in AQP1 proteoliposomes [$P_f$ =0.054±0.008 (SD) cm/s at 37° C.] as compared with control liposomes [$P_f$=0.0097±0.004 (SD) cm/s at 37° C.]. Similar results were obtained despite differences in RBC source and purification procedure. Protein and phospholipid determinations revealed that two independent preparations contained approximately 220 AQP1 monomers per proteoliposome (211 and 233 in two measurements). Therefore, the osmotic water permeability of each protein molecule was $11.7 \pm 1.8 \times 10^{-14}$ cm$^3$/s. On the basis of the calculated AQP1 $P_f$, the AQP1-mediated osmotic water permeability of a human RBC was estimated [0.017 cm/s=[( $11.7 \times 10^{-14}$ cm$^3$/s per AQP1) $2 \times 10^5$ AQP1 monomers/RBC]/($1.4 \times 10^{-6}$ cm$^2$/RBC, the surface area of the human RBC)]. This value is in agreement with the observed $P_f$ of human RBCs (0.02 cm/s) (Finkelstein, 1986, *Water movement through lipid bilayers, pores, and plasma membranes, theory and reality*, John Wiley and Sons, New York, N.Y.; Macey, 1984, *Am. J. Physiol.* 246:C195–C203), indicating that nearly all AQP1 proteins in the proteoliposomes are functional, regardless of their topological orientation. In addition, the ability of AQP1 to conduct water does not appear to require the specialized lipid composition or bilayer structure of the RBC.

Figure 11:
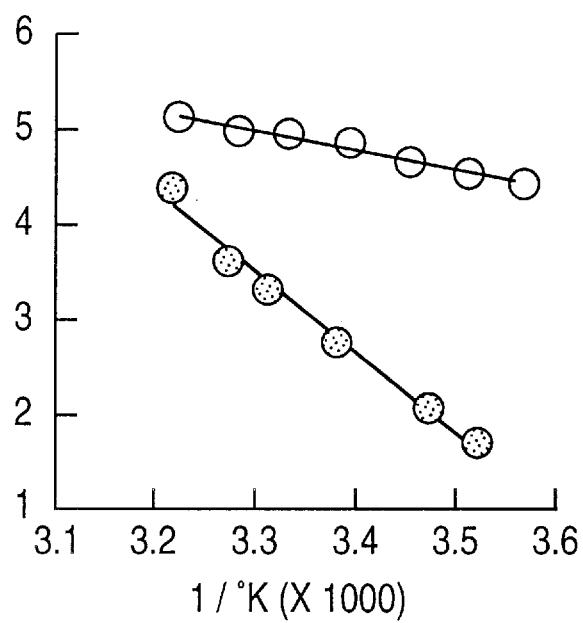
FIG. 11 shows the activation energies in control and AQP1-containing proteoliposomes.

FIG. 11 shows the activation energies of water flow in control (■) and AQP1 (□) proteoliposomes. When $P_f$ measurements in AQP1 proteoliposomes or control liposomes were performed at varying temperatures, Arrhenius activation energies ($E_a$) of 3.1±0.5 and 16.0±1.1 kcal/mol, respectively, were obtained. The low $E_a$ exhibited by AQP1 proteoliposomes agrees well with values reported for intact RBC and RBC membranes (3.2–4.1 kcal/mol; Finkelstein, 1986, *Water movement through lipid bilayers, pores, and plasma membranes, theory and reality*, John Wiley and Sons, New York, N.Y.; Macey, 1984, *Am. J. Physiol.* 246:C195–C203; Zeidel et al., 1992, *Biochemistry* 31:589–596).

Example 7

Figure 12A:
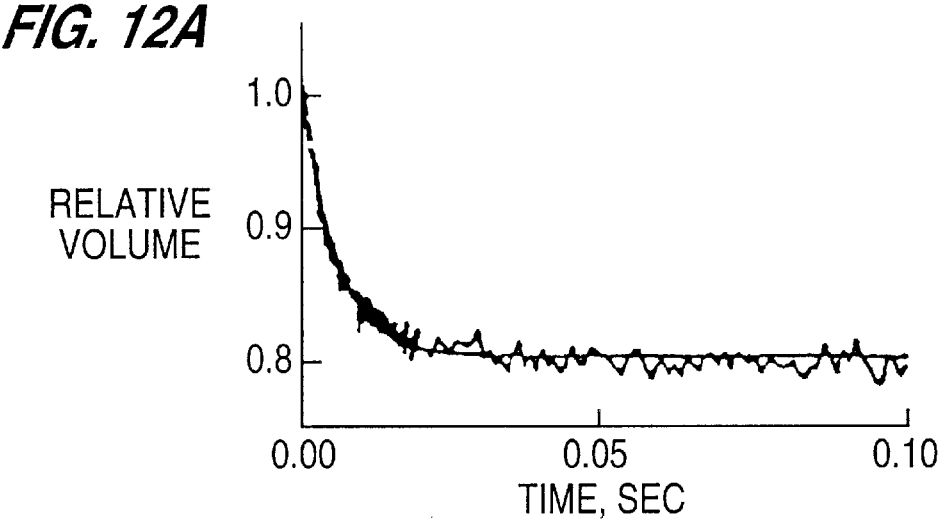
FIGS. 12A–C shows the effect of mercural reagents on water flux an AQP1-contaning proteoliposomes.
Figure 12B:
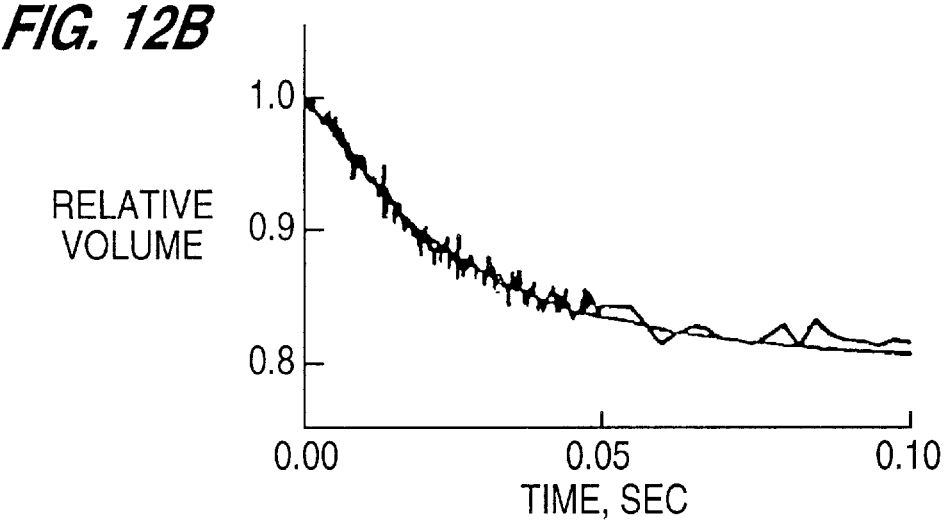
Figure 12C:
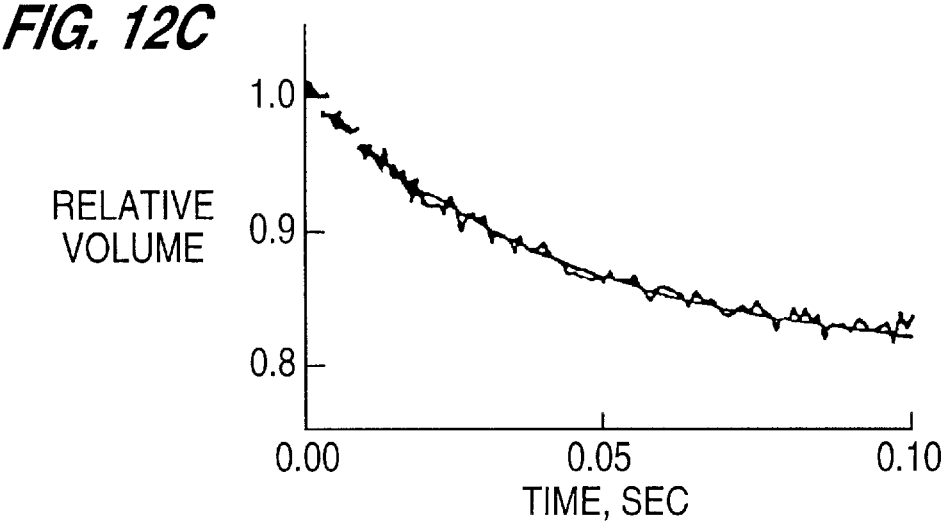

Effect of mercural reagents. FIG. 12 shows the effect of mercural reagents on water flux in CHIP28 proteoliposomes. FIG. 12A shows untreated CHIP28 proteoliposomes. FIG. 12B shows the effect of 1 mM of pCMBS, an organic mercurial, for 25 minutes at 37° C. FIG. 12C shows the effect of 1 mM HgCl$_2$ for 3 minutes at 37° C.

Both 1 mM pCMBS, and 1 mM HgCl$_2$ markedly inhibited $P_f$ in CHIP28 proteoliposomes, reducing these values to 0.009±0.005 cm/s for pCMBS and 0.007±0.003 cm/s for HgCl$_2$. These values are similar to those obtained in control liposomes. Inhibition by pCMBS was partial at 5 and 10 minutes and complete at 20–30 minutes at 37° C. By contrast, HgCl$_2$ inhibition was complete within 5 minutes. Neither pCMBS nor HgCl$_2$ had any effect on the $P_f$ of control liposomes. Inhibition by both mercurial reagents was completely reversed by treatment with the sulfhydryl reagent, β-mercaptoethanol (5 mM). The time courses for inhibition of $P_f$ and reversal of inhibition in CHIP28 proteoliposomes both resemble and kinetics for intact RBC (Macey, 1984, *Am. J. Physiol.* 246:C195–C203; Zeidel et al., 1992, *Biochemistry* 31:589–596).

Example 8

Early studies of water and small nonelectrolyte preferabilities of RBC suggested that small nonelectrolytes may cross the membrane via the water channel (Goldstein & Solomon, 1960, *J. Gen. Physiol.* 44:1–22). Phloretin, however, inhibits urea flux in human RBC without altering water flux. Moreover, water and urea transport can be dissociated in phylogeny. For example, duck RBCs exhibit high water and low urea permeabilities, whereas amphiuma RBCs exhibit low water and high urea permeabilities (Finkelstein, 1986, *Water movement through lipid bilayers, pores, and plasma membranes, theory and reality*, John Wiley and Sons, New York, N.Y.; Macey, 1984, *Am. J. Physiol.* 246:C195–C203).

Exclusion of urea. To determine the selectivity of the CHIP28 water channel, CHIP28-containing liposomes were loaded with urea at a level similar to the measured $K_m$ for urea transport in RBCs and were abruptly mixed with solutions of identical osmolality containing half the urea concentration. Urea permeability was determined by monitoring the relative fluorescence of entrapped carboxyfluorescein during the urea efflux. Solutions inside and outside the vesicle were of equal osmolality but differed in the concentrations of permeant and impermeant solutes (Grossman et al., 1992, *Am. J. Physiol.*, in press). Thus, internal urea concentration was 374 mM and external urea concentration was 187 mM with the remaining osmolality balanced by 187 mM sucrose. Under these conditions, the permeant solute effluxes down its concentration gradient from inside to outside the vesicles; this flux creates an osmotic gradient, leading to efflux of water, increased carboxyfluorescein concentration within the vesicles, and additional carboxyfluorescein self-quenching.

Figure 13A:
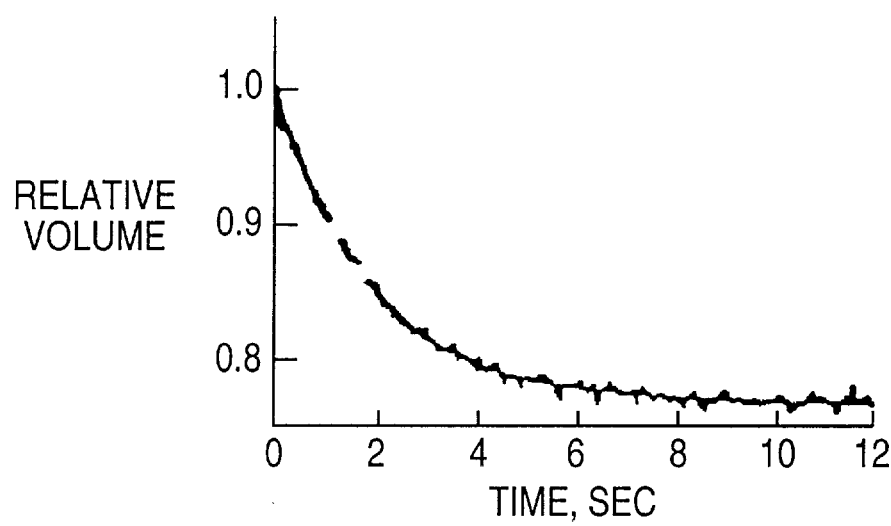
FIG. 13A and 13B show urea fluxes in control liposomes and AQP1-containing proteoliposomes, respectively.
Figure 13B:
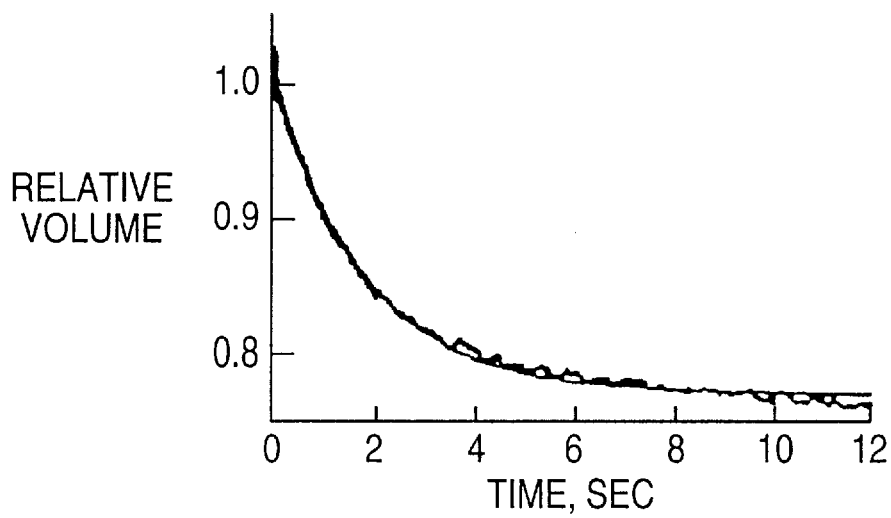

FIG. 13A and B show urea fluxes in control liposomes and CHIP28 proteoliposomes, respectively. As the urea diffused down its concentration gradient, water efflux occurred, leading to further self-quenching of CF fluorescence. As can be seen in FIG. 13, unlike water permeability, the presence of functional CHIP28 did not augment urea permeability. Thus, the CHIP28 water channel excludes urea.

Exclusion of protons. Although the gramidicin channel conducts water and protons rapidly, inhibitor studies in intact RBC suggest that the RBC water channel does not conduct protons (Finkelstein, 1986, *Water movement through lipid bilayers, pores, and plasma membranes, theory and reality*, John Wiley and Sons, New York, N.Y.; Macey, 1984, *Am. J. Physiol.* 246:C195–C203). To test this in CHIP28 proteoliposomes, the extravesicular pH was abruptly lowered from 7.42 to 6.80 and the rate of proton flux monitored (Harris et al., 1990, *Am. J. Physiol.* 259:F366–F371). Proton permeability was measured in CHIP28-containing liposomes containing 150 mM KCl and 5 mM MOPS, incorporating 1 μM valinomycin to prevent accumulation of protons from generating a positive intravesicular voltage. Vesicles at pH 7.40 were abruptly exposed to a solution of pH 6.80, and the time course of the fall in intravesicular pH was followed on the stopped-flow device by monitoring the quenching by protons of 0.5 mM entrapped carboxyfluorescein. Over the pH range employed, fluorescence was linearly related to pH; extravesicular fluorescence was quenched with anti-fluorescein antibody. To ensure that increases in $P_{H+}$ caused by CHIP28 could have been detected, 1 μM gramicidin A was added and increased $P_{H+}$ by over 50-fold in each experiment. The ethanol vehicle used for valinomycin and gramicidin did not alter the high $P_f$ of CHIP28-containing proteoliposomes (Harris et al., 1990, Am. J. Physiol. 259:F366–F371). The proton permeability, $P_{H+}$, was comparable in CHIP28 proteoliposomes (0.0068±0.003 cm/s at 37° C.) and control liposomes (0.0063±0.0004 cm/s), indicating that the CHIP28 channel does not conduct protons.

Example 9
Isolation of a cDNA from Salivary Gland

The most conserved sequences of the Aquaporins were used to design degenerate oligonucleotide primers, and a cDNA library from rat submandibular gland was the template for polymerase chain amplification.

cDNA Cloning—Rat submandibular gland mRNA (1 μg) was reverse-transcribed using random hexamer primers and reverse transcriptase (Perkin-Elmer Cetus). Nested, degenerate oligonucleotide primers were designed corresponding to the most highly conserved sequences surrounding the NPA motifs in the Aquaporins (Reizer et al., 1993, Crit. Rev. Biochem. Mol. Biol., 28:235–257; Preston, 1993, in Methods in Molecular Biology (White, B. A., ed) Vol. 15, pp. 317–337, Humana Press, Totowa, N.J.); sense primers MDU-1 (5'-STBGGNCAYRTBAGYGGNGC-NCA-3') and MDU-2 (5' GGGATCCGCHCAYNTNAAYCCHGYN-GTNAC-3'), antisense primers MDD-1 (5'GCDGRNSCVARD-GANCGNGCNGG-3') and MDD-2 (5'-CG GAATTCGDGCDGGRTTNATNSHNSMNCC-3'). The reverse-transcribed RNA was amplified by 30 cycles of polymerase chain reaction (1 min at 94° C., 1 min at 52° C., 1 min at 72° C.) using 100 pmol of MDU-1 and MDD-1; the products were reamplified using 100 pmol of MDU-2 and MDD-2.

The 376-bp product was used to isolate two positive plaques from the same library. A 376-bp product was ligated into the EcoRV site of pBS-KS(+) for bacterial transformation. This DNA fragment was radiolabeled with [α-$^{32}$P] dCTP (3,000 Ci/mmol, Amersham) and used to probe nylon membranes (Colony/Plaque Screen, DuPont NEN) containing 2×10$^5$ plaques from an adult Sprague-Dawley rat submandibular gland cDNA library in ZAP II (Girard et al., 1993, J. Biol. Chem., 268:26592–26601). Membranes were hybridized for 18 h with 10$^6$ cpm/ml of probe, and washed at 65° C. in 0.2×SSC, 0.1% SDS. A 1.5-kb insert from a purified plaque was subcloned for double-stranded dideoxy-nucleotide sequencing with Sequenase 2.0 (U.S. Biochemical) and [α-$^{35}$S]dATP (1,000 Ci/mmol).

The 1.5-kb insert in plasmid AQP5 (the sequence was cut from the lambda library and ligated into pBLUESCRIPT) contained a 109-bp 5' untranslated sequence preceding an initiation site consensus (Kozak, 1987, Nucleic Acids Res., 15:8125–8132). A 795-bp open reading frame was followed by 3'-untranslated sequence containing a polyadenylation consensus (FIG. 14A).

Figure 14B:
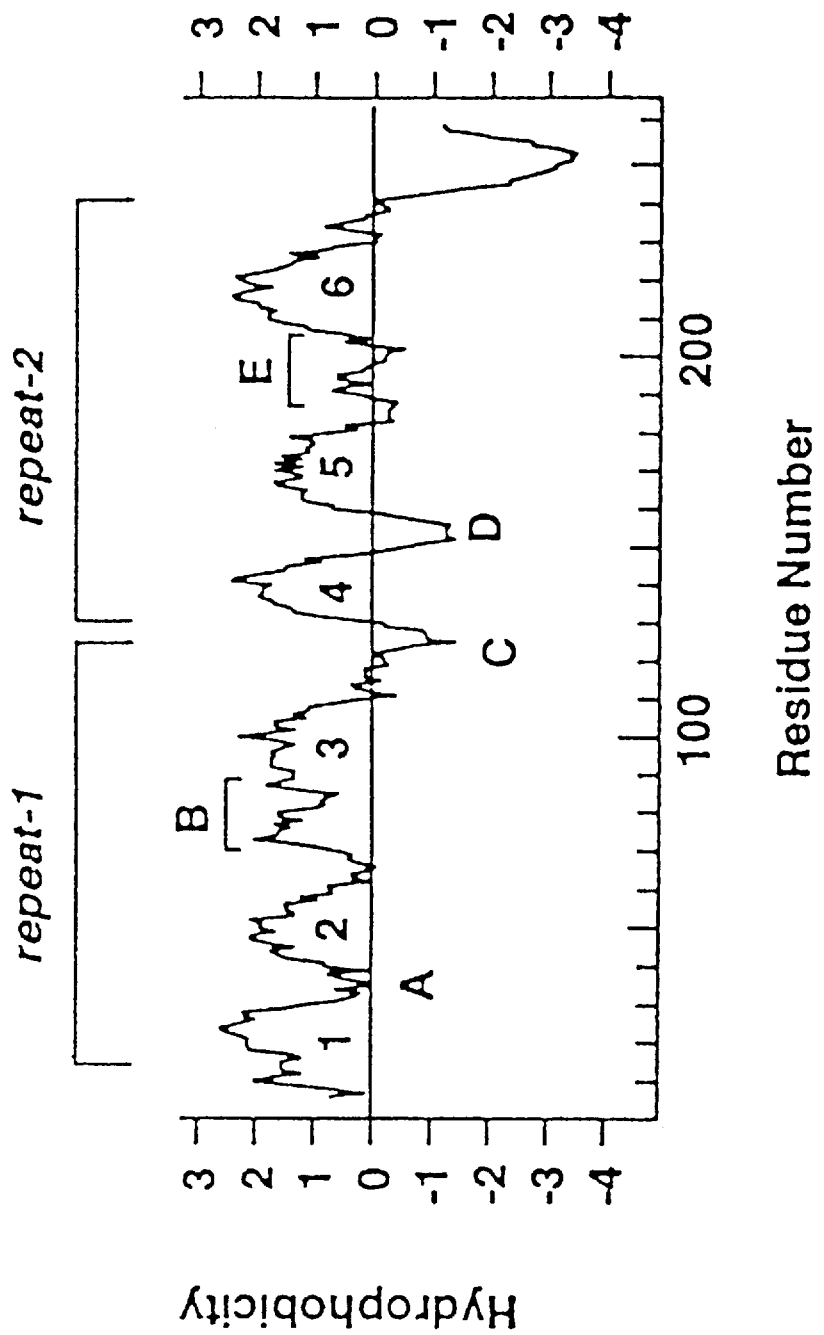
FIG. 14 A–C show the nucleotide sequence and deduced amino acid sequence of the clone AQP5 SEQ ID NO:18(A), isolated from a rat submandibular gland cDNA library, along with sequence analysis (B) and predicted topology of salivary cDNA(C).
Figure 14C:
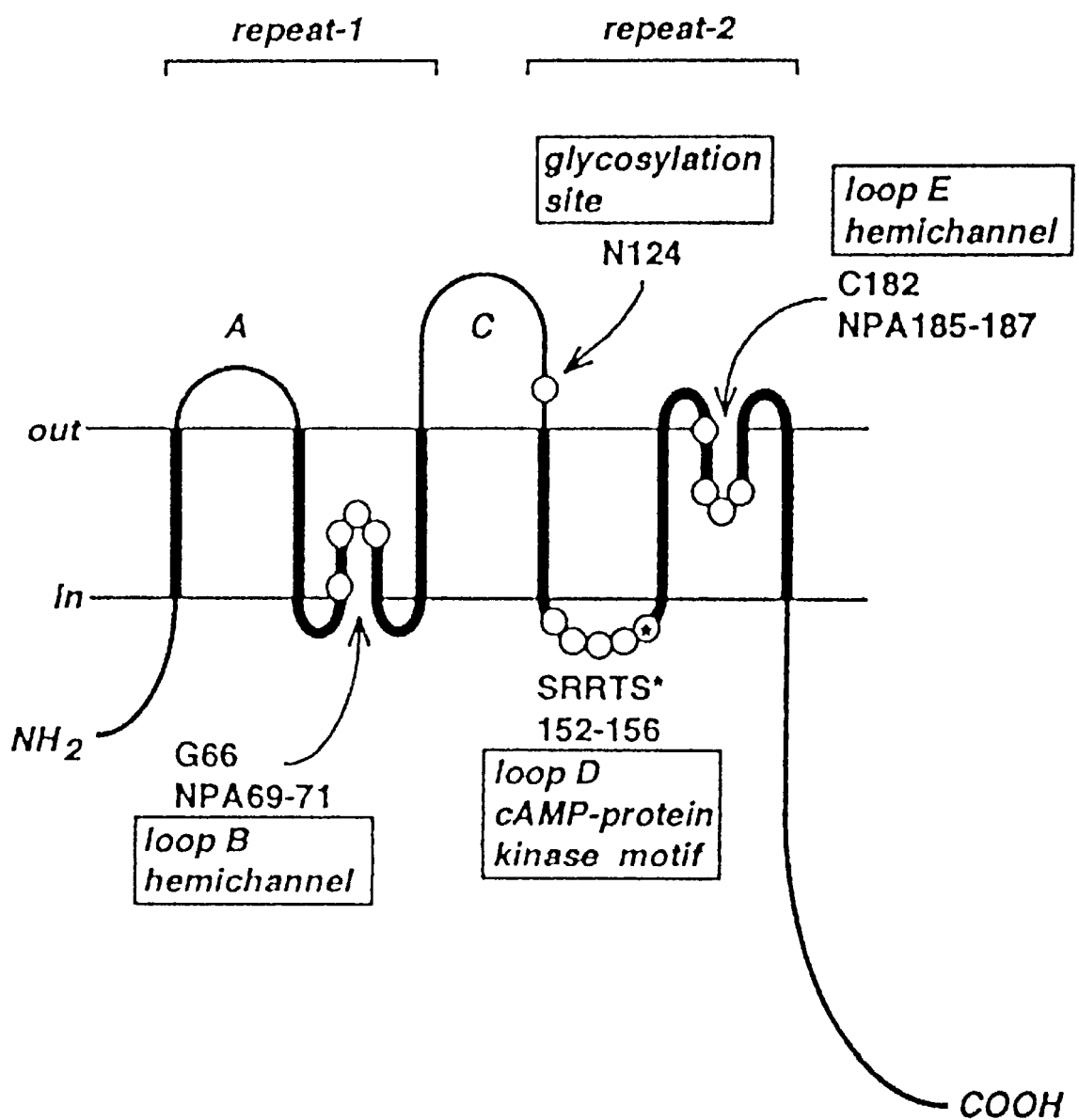

Deduced Structure of the Salivary Polypeptide—Analysis of the GenBank data base revealed the salivary cDNA to be a novel member of the Aquaporin family. The open reading frame encodes a polypeptide of amino acids. Hydropathy analysis confirmed six putative bilayer-spanning domains and five connecting loops of which loops B and E were also hydrophobic (FIG. 14B). Loops B and E each contained the recognized NPA motif (Asn-Pro-Ala) present in all Aquaporins; the 2nd NPA was flanked by a cysteine at residue 182 (FIG. 14C) corresponding to the known mercurial-inhibitory site of AQP1 (Preston et al., 1993, J. Biol Chem., 268:17–20). The deduced protein was 45% identical overall with AQP1, with the highest levels of homology in the six bilayer-spanning domains and loops B, D, and E (FIG. 14C). Two N-glycosylation consensus sites were identified at residues Asn-124 and Asn-125 in loop C., supporting the extracellular location of this domain as predicted by topology mapping (Preston et al., 1994b, J. Biol. Chem., 269:1668–1673) and consistent with potential N-glycosylation sites in AQP2 (Fushimi et al., 1993), AQP3 (Ishibashi e w al., 1994), and AQP4 (Hasegawa et al., 1994; Jung et al., 1994a). Although cytoplasmic loop D is predicted to be only 8 residues long, it contains the sequence Ser-Arg-Arg-Thr-Ser, matching the consensus for cAMP-protein kdnase phosphorylation (Kennelly and Krebs, 1991, J. Biol. Chem., 266:15555–15558), a motif present also in the COOH-terminal domain of AQP2 (Fushimi et al., 1993).

FIG. 14A shows the sequence analysis and predicted topology of salivary cDNA, based on the nucleotide sequence and deduced amino acid sequence of the clone AQP5.A, isolated from a rat submandibular gland cDNA library. Presumed bilayer spanning domains are underlined, and adjacent putative N-glycosylation sites are identified (*). Conserved NPA motifs and mammalian cAMP-protein kinase motifs are enclosed. A polyadenylation consensus is double-underlined. FIG. 14B shows hydropathy analysis of deduced amino acid sequence using a 7-residue window (Kyte, J., and Doolittle, R. F., 1982, J. Mol. Biol., 105:105–132). FIG. 14C shows proposed membrane topology based upon sequence analysis and hourglass model for Aquaporins (Preston et al., 1994b; Jung et al., 1994b, J. Biol. Chem., 269:14648–14654) comprised of six bilayer-spanning domains and five connecting loops (A–E). Domains with 40–65% of residues identical with AQP 1 (CHIP) are represented as heavy lines (bilayer spanning domains and loops B, D, end E); domains and loops with ≦25% identity are thin lines (NH$_2$- and COOH termini; loops A and C). Locations of selected residues are identified: N-glycosylation site, NPA motifs in the first and second aqueous hemichannels, residues corresponding to mercury-sensitive sites in AQP1, cAMP-protein kinase motif.

Table 3 shows sequence comparison of members of the mammalian Aquaporin protein family.

TABLE 3

Comparison of AQP 5 Sequence to the Sequence of Other Members of the Mammalian Aquaporin Protein Family

| Aquaporin | % Identity With AQP5 Sequence | Physiologic Locality |
| --- | --- | --- |
| AQP5 | 100 | Salivary, Lacrimal, Pulmonary Tissues |
| AQP2 (CD) | 63 | Renal Collecting Ducts Vasopressin-Regulated |
| MIP | 49 | Lens Fiber Cells |
| AQP4 | 49 | Brain Hg-insensitive |
| AQP1 (CHIP) | 45 | Red Cells Renal Proximal Tubules |
| AQP3 | 29 | Renal Collecting Duct Basolateral Membranes |

The amino acid sequences of human AQP1 (Preston and Agre, 1991, Proc. Natl. Acad. Sci. U.S.A., 88:11110–11114), bovine MIP (Gorin et al., 1984), and rat AQP2 (Fushimi, et al., 1993), AQP3 (Ishibashi, et al., 1994), AQP4 (Jung, et al., 1994a), and AQP5 (FIG. 1) were aligned by the PILEUP program (version 7.1, Genetic Computer Group, Madison Wis.) of progressive alignments (Feng and Doolittle, 1990, Methods Enzymol., 183:375–387) using a gap weight of 3.0 and gap length of 0.1 running on a VAX computer system. The percentage amino acid identity between AQP5 and each of the Aquaporins is represented.

Example 10

Expression In vitro

Protein synthesis from the salivary cDNA was demonstrated with a cell-free translation system.

Expression in vitro—In vitro-transcribed cRNA (200 ng) was added to a rabbit reticulocyte lysate mixture (Promega) containing [$^{35}$S]methionine and canine pancreatic microsomes. The reaction was incubated for 1 h at 30° C., and the microsomes were pelleted at 100,000×g for analysis by SDS-PAGE autoradiography.

Cell-free translation of the cRNA encoding AQP1 (CHIP) in the presence of microsomes yielded a band at 28 kDa by SDS-polyacrylamide gel electrophoresis and slightly larger bands corresponding to glycosylated polypeptides; similar translation of the salivary cRNA yielded a major band at 27 kDa. This corresponds to the predicted mass of 28.4 kDa with slightly more rapid electrophoretic mobility probably resulting from a larger number of hydrophobic residues (Helenius and Simons, 1975, Biochim. Biophys. Acta, 415:29–79).

Example 11

Expression and Transport Function In Vivo

Transmembrane water flow through the salivary water channel protein was evaluated by expression in Xenopus oocytes.

Functional expression in Oocytes—A 1-kb BamHI fragment containing the 5' untranslated sequence and the entire open reading frame of the salivary cDNA was blunt-end-ligated into the BglII site of the Xenopus expression construct pXβG, which contains the HindIII-Pst insert of pSP64T in pBS II KS (Preston et al., 1992, Science, 256:385–387). Capped cRNA was synthesized in vitro after digestion with XbaI (Preston et al., 1993). Defolliculated stage V–VI Xenopus oocytes were injected with 50 nl of water or up to 5 ng of sample cRNAs and incubated for 3 days at 18° C. in 200 mosM modified Barth's buffer. The oocytes were transferred to 70 mosM modified Barth's buffer at 21° C.; oocyte swelling was monitored by videomicroscopy, and the coefficient of osmotic water permeability ($P_f$) was determined (Preston et al., 1992, 1993). Uptake of [$^{14}$C]urea or [$^{14}$C]glycerol was measured by incubating oocytes in 200 mosM Barth's buffer for 10–20 min at 21° C. followed by washing and SDS solubilization. No increase in ion conductance was found when control oocytes were compared to RNA-injected oocytes by two electrode voltage clamps (Preston et al, 1992).

FIG. 15 shows osmotic water permeability ($P_f$) of oocytes injected with 50 nl of water without RNA or oocytes injected with 5 ng of the indicated cRNAs. Shown are the mean values and standard deviations of 4–5 oocytes receiving no further treatment (stippled bars), oocytes incubated for 5 min. in 1 mM HgCl$_2$ (black bars), or oocytes incubated for 5 min. in 1 mM HgCl$_2$ (black bars), or oocytes incubated for 5 min. in 1 mM HgCl$_2$ followed by 30 min. in 5 mM β-mercaptoethanol (open bars). Similar to oocytes injected with AQP1 cRNA, injection of oocytes with the salivary cRNA increased the $P_f$ by approximately 20-fold (FIG. 15). Therefore, the salivary protein qualifies as the 5th mammalian member of the Aquaporin family of water channels (Agre et al., 1993b, Am. J. Physiol., 265:F461), and the gene has been designated Aquaporin-5 (symbol AQP5) by the Genome Data Base.

The increase in $P_f$ mediated by expression of AQP1 is blocked by treatment with 1 mM HgCl$_2$ and restored by incubation in β-mercaptoethanol (FIG. 15; Preston et al., 1992). Similar treatment of oocytes expressing AQP5 with 1 mM HgCl$_2$ produced a comparable reduction in $P_f$ which was restored by incubation with β-mercaptoethanol (FIG. 15). Likewise, oocytes expressing AQP5 exhibited no increase in the membrane transport of [$^{14}$C]urea or [$^{14}$C]glycerol above that of water-injected oocytes, and electrophysiological studies failed to reveal increased membrane conductance (not shown).

Example 12 tissue Distribution of AQP5 mRNA

Northern Blots—RNA was isolated from various rat tissues using RNazol B solution (Cinna Scientific). Aliquots of total RNA or poly(A)-RNA were resolved on a formaldehyde agarose gel, transferred to nylon membranes, and hybridized at high stringency with the full-length salivary cDNA probe labeled with [α-$^{32}$P]dCTP as described (Preston and Agre, 1991). Total RNA (10 μg) or poly(A)-RNA (1 μg) from submandibular gland., sublingual gland, and other indicated rat tissues hybridized with $^{32}$P-labeled probe corresponding to full-length AQP5 cDNA. Equivalent amounts of RNA were loaded as verified by the abundance of 18 S and 28 S RNAs and Northern analysis using a mouse γ-actin probe (not shown).

Total RNA or poly(A)-RNA from rat salivary glands showed a single prominent band of approximately 1.6 kb, and analyses of RNA from lacrimal gland, trachea, eye, and distal lung were similar. In contrast, no signal was detected with the AQP5 probe when comparable amounts of RNA from kidney, brain, intestine, or other tissues were analyzed (FIG. 16).

In Situ Hybridizations—Cryosections of 12 μm were cut from rat submandibular gland and eye, fixed with 4% paraformaldehyde in phosphate-buffered saline, and treated with 0.25% acetic anhydride, 0.1M triethanolamine for 10 min. [$^{35}$S]UTP-labeled antisense and sense riboprobes were made with T$_7$ or T$_3$ RNA polymerase from the 1-kb BamHI DNA fragment (see above). Sections were hybridized overnight at 56° C. with 10$^6$ cpm of probe. After RNase treatment, sections were exposed to autoradiographic film for 1 day and to photographic emulsion for 4 days (Bhat et al., 1994, Neurosci., 14:3059–3071).

Figure 17B:
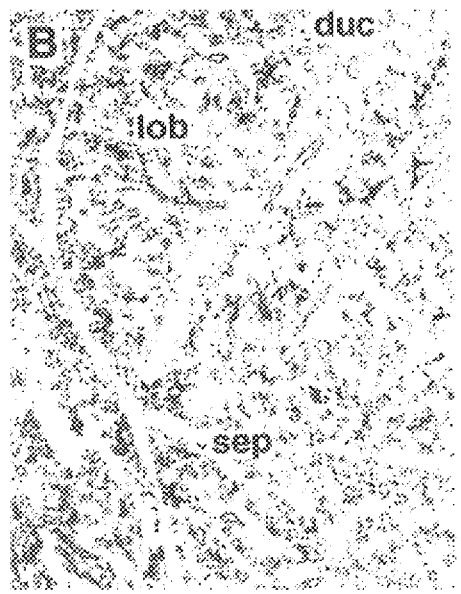
FIG. 17A, A',A", B and B', B" shows in situ localization of AQP5 mRNA in rat eye (A and A') and submandibular salivary gland (B and B').
Figure 17B:
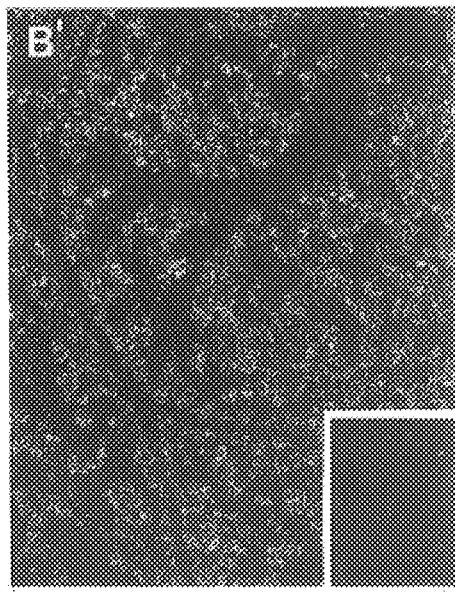

FIG. 17 shows in situ localization of AQP5 mRNA in rat eye and submandibular salivary gland. FIG. 17A and A' show bright field and dark field views, respectively, of a section of eye examined by in situ hybridization with antisense probe revealing intense signal over corneal epithelium (epi) but not over corneal endothelium (end), ciliary body (cil), iris (ir), or other structures. FIG. 17B and B' show bright field and dark field views, respectively, of a section of submandibular gland examined by in situ hybridization with antisense probe revealing intense signal over secretory lobules (lob) but not over excretory ducts (duc) or stromal septae (sep). Parallel incubations with sense probes failed to demonstrate hybridization in cornea or submandibular gland even after prolonged autoradiographic exposure (insets). Magnifications ×45.

In situ hybridizations of eye with an antisense AQP5 riboprobe revealed a discrete pattern of expression over the corneal epithelium, whereas the sense riboprobe gave a negligible signal (FIG. 17A). This pattern of localization contrasted with that of other Aquaporin transcripts in eye. Corneal endothelium, lens epithelium, and nonpigmented epithelium of ciliary body and iris are known to express AQP1 (Nielsen et al., 1993b); however, none were found to express AQP5 (FIG. 17A and other data not shown). Lens fiber cells are known to express large amounts of the homolog major intrinsic protein, MIP (Gorin et al., 1984), but no AQP5 hybridization was detected (not shown). Neither the retinal neuronal nuclear layer, which expresses AQP4 (Hasegawa et al., 1994), nor retinal pigmented epithelium gave specific AQP5 signals (not shown).

In situ hybridizations of salivary glands also revealed discrete hybridization patterns. Submandibular glands contain serous and mucus-secreting epithelia within the glandular lobules. Strong hybridization was identified over the secretory lobules, whereas only background levels of hybridization were detected over the stromal septae and excretory ducts (FIG. 17B). Specificity of these hybridizations was confirmed by control studies with sense riboprobes which failed to hybridize (FIG. 17B, insert). Distribution of AQP5 mRNA was similar in parotid and sublingual salivary glands and lacrimal glands (not shown).

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, hybridoma technology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

I claim:

1. An isolated DNA molecule which encodes a water channel protein corresponding to the amino acid sequence of Aquaporin-5 (AQP5) as shown in SEQ ID NO:19.

2. The DNA molecule of claim 1 which has a nucleotide sequence as shown in SEQ ID NO:18 and encoding AQP5.

3. A recombinant vector comprising the nucleotide sequence of the DNA molecule of claim 1.

4. The recombinant vector of claim 3, wherein the vector is an expression vector.

5. A method of preparing a water channel protein comprising transforming a host cell with the expression vector of claim 4, growing the host cell in a culture medium to express AQP5, and recovering AQP5.

* * * * *